United States Patent
Canich

(10) Patent No.: US 6,617,466 B1
(45) Date of Patent: Sep. 9, 2003

(54) MONOCYLOPENTADIENYL TRANSITION METAL OLEFIN POLYMERIZATION CATALYSTS

(75) Inventor: Jo Ann Marie Canich, Webster, TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

(21) Appl. No.: 07/844,813

(22) Filed: Mar. 2, 1992

Related U.S. Application Data

(60) Division of application No. 07/581,841, filed on Sep. 13, 1990, now Pat. No. 5,096,867, which is a continuation-in-part of application No. 07/533,245, filed on Jun. 4, 1990, now Pat. No. 5,055,438, which is a continuation-in-part of application No. 07/406,945, filed on Sep. 13, 1989, now abandoned.

(51) Int. Cl.$^7$ .............. C07F 17/00; C07F 7/00; B01J 31/00
(52) U.S. Cl. .............. 556/11; 556/12; 556/21; 556/53; 502/103; 502/117; 526/160; 526/943
(58) Field of Search .............. 556/11, 12, 21, 556/53; 502/103, 117; 526/160, 943

(56) References Cited

U.S. PATENT DOCUMENTS

| | | | | |
|---|---|---|---|---|
| 5,621,126 A | * | 4/1997 | Canich et al. | 502/152 |
| 5,631,391 A | * | 5/1997 | Canich | 502/103 |
| 5,955,625 A | * | 9/1999 | Canich | 502/152 |

OTHER PUBLICATIONS

M. Reetz, *Organotitanium Reagents in Organic Synthesis*, pp. 117 and 121 (Springer–Verlay 1986).
Kukenhohner, "Untersuchungen zur Darstellung Chiraler Organotitan (IV)—Verbindungen fur Enantioselektire Synthesen" (1983) (unpublished Diplomarbeit, University of Marburg, Germany).
KukenHohner, Organotitan (IV) Agentien: Komplexe Chiraler Chelatliganden und Enantioselektire c–c– Verknupfungen (University of Marburg, Germany 1986).
Final Decision, dated Sep. 28, 2001 ('067 Interference Paper No. 394).
Judgment, dated Sep. 28, 2001 ('067 Interference Paper No. 395).
Interference Telephone Record, dated Nov. 19, 2001 ('067 Interference Paper No. 396).
Decision on Preliminary Motions, dated May 1, 1996 ('067 Interference Paper No. 168).
Decision Redeclaring Interference No. 103,067, dated May 1, 1996 (Paper No. 20).
Junior Party Canich's Opening Final Hearing Brief, dated Aug. 5, 1997, pp. cover, vii–x, 151–233 and Appendix B ('067 Interference Paper No. 319).
Senior Party Stevens Et al.'s Final Hearing Brief, dated Oct. 7, 1997, pp. cover, vi–vii, xxiii–xxiv, 116–168, 193–194 and Appendix C ('067 Interference Paper No. 325).
Junior Party Caniche's Final Hearing Replay Brief, dated Dec. 18, 1997, pp. cover, i, vii–ix, 9–10 and 133–191 ('067 Interference Paper No. 348).
Junior Party Canich's Opening Final Hearing Brief (Redacted Version), dated Oct. 29, 1999, pp. cover, vii–x, 151–233 and Appendix B ('067 Interference Paper No. 377).
Senior Party Stevens Et Al.'s Final Hearing Brief (Redacted Version), dated Dec. 3, 1999, pp. cover, vi–vii, xxiii–xxiv, 116–168 (redacted) and Appendix C ('067 Interference Paper No. 380).
Junior Party Canich's Final Hearing Reply Brief (Redacted Version), dated Jan. 31, 2000, pp. cover, i, vii–x, 9–10, 133–191 (redacted) ('067 Interference Paper No. 382).
Dissertation of Thomas Kükenhöhner, "Organotitan(IV)–Agenitien: Komplexe Chiraler Chelatliganden und Enantioselektive C—C–Verknopfungen" (University of Marburg, Germany 1986) ('067 Interference CX 1023 (German) and CX 1228 (English translation)) (Organotitanium (IV) Agents: Complexes with Chiral Chelate Ligands and Enantioselective C—C Bonds).
Thomas Kükenhöhner, "Untersuchungen zur Darstellung Chiraler Organotitan(IV)–Verbindungen für Enantioselektive Synthesen" (unpublished Diplomarbeit, University of Marburg, Germany) ('067 Interference SX 1049 (German) and SX 1051 (English translation)) (Study on the preparation of chiral organotianium (IV) compounds for enantio–selective synthesis).
M. Reetz, *Organotitanium Reagents in Organic Synthesis*, pp. 117, 121 (Springer–Verlag 1986) ('067 Interference SX 1048).
Okuda, "Synthesis and Complexation of Linked Cyclopentadienyl–Amido Ligands," *Chem. Berg.*, 123 (1990) 1649–51 ('067 Interference CX 1107).
Stevens et al. U.S. Patent No. 5,064,802, "Metal Complex Compounds," filed Jul. 3, 1990 as a continuation–in–part of S.N. 407,169, filed Sep. 14, 1989 ('067 Interference CX 1120).
Shapiro et al,. "[($\{\eta^5$–$C_5Me_4$)$Me_2Si(\eta^1$–$NCMe_3$)\}$(PMe_3)$ScH$]_2$: A Unique Example of a Single–Component α–Olefin Polymerization Catalyst," *Organometallics*, 9 (1990) 867–869 ('067 Interference SX 1164).
Manzer, "Improved Synthesis of Chlorodicyclopentadienyl Derivatives of Scandium (III), Titanium (III) and Vanadium (III)," *J. Organometal. Chem.*, 110 (1976) 291–294 ('067 Interference SX 1180).

(List continued on next page.)

*Primary Examiner*—Porfirio Nazario-Gonzalez

(57) ABSTRACT

The invention is a catalyst system including a Group IV B transition metal component and an alumoxane component which may be employed to polymerize olefins to produce a high molecular weight polymer.

21 Claims, No Drawings

OTHER PUBLICATIONS

Holton et al., "Alkyl–bridged Complexes of the d– and f–Block Elements. Part 1, Di–µ–alkyl–bis(η–cyclopentadienyl)metal(III)–dialkyl aluminum(III) Complexes and the Crystal and Molecular Structure of the Ytterbium Methyl Species," *J. Chem Soc., Dalton Trans.*, (1979) 45–53 ('067 Interference SX 1181).

Brintzinger et al., Synthesis and Crystal Structure of a Chiral ansa–Zirconocene Derivative with Ethylene–Bridged Tetrahydroindenyl Ligands, *J. Organometal. Chem.*, 288 (1985) 63–67 ('067 Interference SX 1017).

Brintzinger et al., "Synthesis and Crystal Structures of Ethylene–Bridged Titanocene and Zirconocene Derivatives with Permethylated Ring Ligands," *J. Organometal. Chem.*, 288 (1985) 69–77 ('067 Interference Exhibit SX 1018).

Brintzinger et al., "Synthesis and Crystal Structure of a Chiral ansa–Titanocene Derivative with Trimethylene–Bridged Tetrahydroindenyl Ligands," *J. Organometal. Chem.*, 322 (1987) 65–70 ('067 Interfrence Exhibit SX 1016).

Teuben et al., "Synthesis and Properties of Aryldicyclopentadienyl– Titanium (III) Compounds," *J. Organometal. Chem.*, 46 (1972) 313–321 ('067 Interference Exhibit SX 1182).

Lappert et al., Amido–derivatives of Metals and Metalloids. Part XIII. Dialkylamides of Low–valent Titanium: their Preparation and Properties,*J. Chem Soc. (A)*, 1971, 874–877 ('067 Interference Exhibit SX 1183).

Basso Bert et al., "A Flouroalkoxy Ligand in Organometallic Chemistry of Titanium (IV): Synthesis and Reactivity of Some Monocyclopentadienyl Fluoroalkoxy Derivatives," *J. Organomeal. Chem.*, 165 (1979) 209–214 ('067 Interfrence Exhibit SX 1053).

Baker et al., "Synthesis and Molecular Structures of Homoleptic Dicyclohexylphosphide Complexes of the Early Transition Metals," *J. Am. Chem. Soc.*, 105 (1983) 6763–6765 ('067 Interference Exhibit SX 1184).

Junior Party Canich's (Contingent) Motion No. 16 Pusuant to 37 C.F.R. §§ 1.633(i) and 1.633(c)(2) to Redefine the Interfering Subject Matter by Adding Application Claims Corresponding to a Count ('067 Interference Paper No. 130), together with Amendment dated Jun. 7, 1993, adding Claims 36–46.

Opposition No. 16—The Party Stevens et al.'s Opposition to the Party Canich's Motion No. 16 to Redefine the Interfering Subject Matter by Adding Application Claims Corresponding to a Count ('067 Interference Paper No. 147).

Junior Party Canich's Reply to Stevens' Opposition to Canich Motion No. 16 ('067 Interference Paper No. 156).

Junior Party Canich's (Contingent) Motion No. 17 Pursuant to 37 C.F.R. §§ 1.633(f) and 1.633(c)(2)(iv) to Be Accorded the Benefit of the Filing Dates of Her Earlier Filed United States Applications ('067 Interference Paper No. 131).

Opposition No. 17—The Party Stevens et al.'s Response to the Party Canich's Motion No. 17 for the Benefit of the Filing Dates of Its Earlier Filed United States Applications ('067 Interference Paper No. 148).

Junior Party Canich's Reply to Stevens' Response to Canich Motion No. 17 ('067 Interference Paper No. 157).

Junior Party Canich's Motion No. 7 Pursuant to 37 C.F.R. § 1.633(c)(2) to Redefine the Interfering Subject Matter by Adding Application Claims Corresponding to a Count ('067 Interference Paper No. 16), together with Amendment dated May 10, 1993 adding Claims 27–35.

Opposition No. 7—The Party Stevens et al.'s Opposition to the Party Canich's Motion No. 7 to Redefine the Interfering Subject Matter by Adding Application Claims Corresponding to a Count ('067 Interference Paper No. 30).

Junior Party Canich's Reply to Stevens Opposition to Canich Motion No. 7 ('067 Interference Paper No. 79).

Junior Party Cinch's Motion No. 9 Pursuant to 37 C.F.R. §§ 1.633(c)(2) and 1.633(i) to Redefine the Interfering Subject Matter by Amending Application Claims Corresponding to a Count ('067 Interference Paper No. 48), together with Amendment dated Jun. 7, 1993 amending Claims 22, 24 and 25.

Opposition No. 9—The Party Stevens et al.'s Opposition to the Party Canich's Motion No. 9 to Redefine the Interfering Subject Matter by Amending Application Claims Corresponding to a Count ('067 Interference Paper No. 84).

Junior Party Canich's Reply to Stevens Opposition to Canich Motion No. 9 ('067 Interference Paper No. 123).

Junior Party Canich's (Contingent) Motion No. 13 Pursuant to 37 C.F.R. § 1.635 for Leave to file a Late Motion and Junior Party Canich's Motion Pursuant to 37 C.F.R. §§ 1.633(c)(2) and 1.633(i) to Redefine the Interfering Subject Matter by Amending Application Claims Corresponding to a Count, and Junior Party Canich's (Contingent) Motion Pursuant to 37 C.F.R. §§ 1.633(f) to be Accorded the Benefit of the Filing Date of Her Earlier Filed United States Applications, ('067 Interference Paper No. 81), together with Amendment dated Jun. 22, 1993 amending Claims 20–30 and 32–33.

Opposition No. 13—The Party Stevens et al.'s Opposition to the Party Canich's Contingent Motion No. 13 (1) Under 37 CFR 1.635 for Leave to file a Late Motion; (2) Under 37 CFR 1.633(c)(2) and 1.633(i) to Redefine the Interfering Subject Matter by Amending Claims Corresponding to a Count; and (3) Under 37 CFR 1.633(f) to be Accorded the Benefit of the Filing Date of Her Earlier Filed United States Applications ('067 Interference Paper No. 106).

Junior Party Canich's Reply to Stevens Opposition to Canich Motion No. 13 ('067 Interference Paper No. 140).

Motion No. 1—The Party Stevens et al.'s 37 CFR 1.633(a) Motion for a Judgment that Claims 22–26 in the Party Canich's Application Are Unpatentable under 35 USC 103 ('067 Interference Paper No. 53).

Junior Party Canich's Opposition to Senior Party Stevens et al.'s Motion No. 1 ('067 Interfrence Paper No. 42).

Reply No. 1—The Party Stevens et al.'s Reply to the Party Canich's Opposition to the Party Stevens et al.'s Motion No. 1 for a Judgment that the Party Canich's Claims 22–26 Are Unpatentable under 35 USC 103 ('067 Interference Paper No. 62).

Motion No. 2—The Party Stevens et al.'s 37 CFR 1.633(a) Motion for a Judgment that Claims 22–26 of the Party Canich's Application Are Unpatentable under the Second Paragraph of 35 USC 112 ('067 Interference Paper No. 54).

Junior Party Canich's Opposition to Senior Party Stevens et al.'s Motion No. 2 ('067 Interference Paper No. 43).

Reply No. 2—The Party Stevens et al.'s Reply to the Party Canich's Opposition to the Party Stevens et al.'s Motion for a Judgment that Claims 22–26 of the Party Canich's Application Are Unpatentable under the Second Paragraph of 35 USC 112 ('067 Interference Paper No. 63).

Motion No. 7—The Party Stevens et al.'s Contingent 37 CFR 1.633(a) Motion for Judgment that Claims 27–30 and 32–35 Proposed by the Party Canich Are Unpatentable under the First and Second Paragraphs of 35 USC 112 ('067 Interference Paper No. 32).
Junior Party Canich's Opposition to Senior Party Stevens et al.'s Belated Motion No. 7 ('067 Interference Paper No. 92).
Reply No. 7—The Party Stevens et al.'s Reply to the Party Canich's Opposition to the Party Stevens et al.'s Motion No. 7 ('067 Interference Paper No. 113).
Motion No. 8—The Party Stevens et al.'s Contingent 37 CFR 1.633(a) Motion for a Judgment that the Party Canich's Claims 27–35 Are Unpatentable under of 35 USc 102 and 103 ('067 Interference Paper No. 33).
Junior Party Canich's Opposition to Senoir Party Stevens et al.'s Belated Motion No. 8 ('067 Interference Paper No. 93).
Reply No. 8—The Party Stevens et al.'s Reply to the Party Canich's Opposition to the Party Stevens et al.'s Motion No. 8 for a Judgment that the Party Canich's Claims 27–35 Are Unpatentable under of 35 USC 102 and 103 ('067 Interference Paper No. 114).
Motion No. 14—The Party Stevens et al.'s Contingent Motion under 37 CFR 1.633(a) for a Judgment that the Party Canich's Claims 22–26 Are Unpatentable to the Party Canich under 35 USC 102(a) and (e) ('067 Interference Paper No. 39).
Junion Party Canich's Opposition to Senior Party Stevens et al.'s Belated Motion No. 14 ('067 Interference Paper No. 99).
Reply No. 14—The Party Stevens et al.'s Reply to the Party Canich's Opposition to the Party Stevens et al.'s Motion for Judgment ('067 Interference Paper No. 120).
Motion No. 17—The Party Stevens et al.'s Contingent 37 CFR 1.633(a) Motion for a Judgment that the Party Canich's Claims 22–26 Are Unpatentable under 35 USC 102(b) and/or 103 ('067 Interference Paper No. 102).
Junior Party Canich's Opposition to Senior Party Stevens et al.'s Motion No. 17 ('067 Interference Paper No. 134).
Reply No. 17—The Party Stevens et al.'s Reply to the Party Canich's Opposition to the Party Stevens et al.'s Motion No. 17 for a Judgment of Unpatentability of the Party Canich's Claims Corresponding to a Count ('067 Interference Paper No. 145).
Motion No. 19—The Party Stevens et al.'s 37 CFR 1.635 Motion Requesting Authorization to File Declarations Clarifying the Prior Art Status of the Party Steven et al.'s Exhibit 85 ('067 Interference Paper No. 162).
Junior Party Canich's Opposition to Senior Party Stevens et al.'s Motion No. 19 ('067 Interference Paper No. 165).
Reply No. 19—The Party Stevens et al.'s Reply to the Party Canich's Opposition to the Party Stevens et al.'s Motion Requesting Authorization to File Declarations Clarifying the Prior Art Status of the Party Steven et al.'s Exhibit 85 ('067 Interference Paper No. 166).

Stevens et al.'s Motion No. 23 for Judgment pursuant to 37 C.F.R. § 1.633(a) on the Ground that Canich's Claims are not Patentable under 35 U.S.C. § 112 for Failure to Disclose the Best Mode ('067 Interference Paper No. 266).
Canich Opposition No. 23 ('067 Interfereance Paper No. 277).
Stevens et al.'s Reply No. 23 ('067 Interference Paper No. 274).
Joint Notice, dated Jul. 8, 1999 ('067 Interference Paper No. 371).
Joint Statement Identifying the Motions that Are Pending Without Opposition and the Motions that Remain in Dispute ('067 Interference Paper No. 375).
Joint Statement Identifying the Motions that the Parties Have Agreed to Withdraw from Consideration ('067 Interference Paper No. 374).
Declaration under 37 CFR 1.639(b) of Tobin Marks, dated May 10, 1993.
Second 37 CFR 1.639(b) Declaration of Tobin Marks, dated Jun. 7, 1993.
Second [sic: Third] 37 CFR 1.639(b) Declaration of Tobin Marks, dated Jun. 22, 1993.
The Party Stevens et al.'s Third [sic: Fourth] Declaration Under 37 CFR 1.639(b) of Tobin Marks, dated Jun. 28, 1993.
The Party Stevens et al.'s Fourth [sic: Fifth] Declaration Under 37 CFR 1.639(b) of Tobin Marks, dated Jun. 29, 1993.
The Party Stevens et al.'s Fifth [sic: Sixth] Declaration Under 37 CFR 1.639(b) of Tobin Marks, dated Jul. 10, 1993.
The Party Stevens et al.'s Sixth [sic: Seventh] Declaration Under 37 CFR 1.639(b) of Tobin Marks, dated Jul. 12, 1993.
The Party Stevens et al.'s Seventh [sic: Eighth] Declaration Under 37 CFR 1.639(b) of Tobin Marks, dated Aug. 11, 1993.
Supplemental Declaration of Terry J. Burkhardt, pp. 1–36 and 62, dated Jun. 7, 1993.
Second Supplemental Declaration of Terry J. Burkhardt, pp. 1–2 and 7–25, dated Jun. 22, 1993.
Third Supplemental Declaration of Terry J. Burkhardt, pp. 1–15 and 22–24, dated Jun. 28, 1993.
Fourth Supplemental Declaration of Terry J. Burkhardt, dated Jul. 13, 1993.
Fifth Supplemental Declaration of Terry J. Burkhardt, dated Jul. 22, 1993.
Sixth Supplemental Declaration of Terry J. Burkhardt, dated Aug. 26, 1993.
'067 Interference Record pp. CR 6163–6174.

* cited by examiner

MONOCYLOPENTADIENYL TRANSITION METAL OLEFIN POLYMERIZATION CATALYSTS

SPECIFICATION

This application is a Divisional of Ser. No. 07/581,841, filed Sep. 13, 1990, now U.S. Pat. No. 5,096,867 which is a Continuation-in-Part of U.S. patent application Ser. No. 07/533,245 filed Jun. 4, 1990, now U.S. Pat. No. 5,055,438 which in turn is a continuation-in-part of U.S. patent application Ser. No. 07/406,945 filed Sep. 13, 1989, now abandoned.

FIELD OF THE INVENTION

This invention relates to certain monocyclopentadienyl metal compounds of a Group IV B transition metal of the Periodic Table of Elements, to a catalyst system comprising a monbcyclopentadienyl Group IV B transition metal compound and an alumoxane, and to a process using such catalyst system for the production of polyolefins, particularly polyethylene, polypropylene and α-olefin copolymers of ethylene and propylene having a high molecular weight. The catalyst system is highly active at low ratios of aluminum to the Group IV B transition metal, hence catalyzes the production of a polyolefin product containing low levels of catalyst metal residue. Titanium species of the catalyst are stable at high pressures in unsupported form, unlike their bis-cyclopentadienyl titanium compound counterparts, and exhibit the ability to catalyze the incorporation of higher α-olein comonomer contents for production of higher molecular weight α-olefin copolymers than analogous zirconium and hafnium species of a monocyclopentadienyl transition metal compound.

BACKGROUND OF THE INVENTION

As is well known, various processes and catalysts exist for the homopolymerization or copolymerization of olefins. For many applications it is of primary importance for a polyolefin to have a high weight average molecular weight while having a relatively narrow molecular weight distribution. A high weight average molecular weight, when accompanied by a narrow molecular weight distribution, provides a polyolefin or an ethylene-α-olefin copolymer with high strength properties.

Traditional Ziegler-Natta catalysts system—a transition metal compound cocatalyzed by an aluminum alkyl—are capable of producing polyolefins having a high molecular weight but a broad molecular weight distribution.

More recently a catalyst system has been developed wherein the transition metal compound has two or more cyclopentadienyl ring ligands—such transition metal compound being referred to as a metallocene—which catalyzes the production of olefin monomers to polyolefins. Accordingly, metallocene compounds of a Group IV B metal, particularly, titanocenes and zirconocenes, have been utilized as the transition metal component in such "metallocene" containing catalyst system for the production of polyolefins and ethylene-α-olefin copolymers. When such metallocenes are cocatalyzed with an aluminum alkyl—as is the case with a traditional type Ziegler-Natta catalyst system—the catalytic activity of such metallocene catalyst system is generally too low to be of any commercial interest.

It has since become known that such metallocenes may be cocatalyzed with an alumoxane—rather than an aluminum alkyl—to provide a metallocene catalyst system of high activity for the production of polyolefins.

The zirconium metallocene species, as cocatalyzed or activated with an alumoxane, are commonly more active than their hafnium or titanium analogous for the polymerization of ethylene alone or together with an α-olefin comonomer. When employed in a non-supported form—i.e., as a homogeneous or soluble catalyst system—to obtain a satisfactory rate of productivity even with the most active zirconium species of metallocene typically requires the use of a quantity of alumoxane activator sufficient to provide an aluminum atom to transition metal atom ratio (Al:TM) of at least greater than 1000:1; often greater than 5000:1, and frequently on the order of 10,000:1. Such quantities of alumoxane impart to a polymer produced with such catalyst system an undesirable content of catalyst metal residue, i.e., an undesirable "ash" content (the nonvolatile metal content). In high pressure polymerization procedures using soluble catalyst systems wherein the reactor pressure exceeds about 500 bar only the zirconium or hafnium species of metallocenes may be used. Titanium species of metallocenes are generally unstable at such high pressures unless deposited upon a catalyst support.

A wide variety of Group IV B transition metal compounds have been named as possible candidates for an alumoxane cocatalyzed catalyst system. Although bis(cyclopentadienyl) Group IV B transition metal compounds have been the most preferred and heavily investigated for use in alumoxane activated catalyst systems for polyolefin production, suggestions have appeared that mono and tris(cyclopentadienyl) transition metal compounds may also be useful. See, for example U.S. Pat. Nos. 4,522,982; 4,530,914 and 4,701,431. Such mono(cyclopentadienyl) transition metal compounds as have heretofore been suggested as candidates for an alumoxane activated catalyst system are mono (cyclopentadienyl) transition metal trihalides and trialkyls.

More recently, International Publication No. WO 87/03887 describes the use of a composition comprising a transition metal coordinated to at least one cyclopentadienyl and at least one heteroatom ligand as a transition metal component for use in an alumoxane activated catalyst system for α-olefin polymerization. The composition is broadly defined as a transition metal, preferably of Group IV B of the Periodic Table, which is coordinated with at least one cyclopentadienyl ligand and one to three heteroatom ligands, the balance of the transition metal coordination requirement being satisfied with cyclopentadienyl or hydrocarbyl ligands. Catalyst systems described by this reference are illustrated solely with reference to transition metal compounds which are metallocenes, i.e., bis (cyclopentadienyl) Group IV B transition metal compounds.

Even more recently, at the Third Chemical Congress of North American held in Toronto, Canada in June 1988, John Bercaw reported upon efforts to use a compound of a Group III B transition metal coordinated to a single cyclopentadienyl heteroatom bridged ligand as a catalyst system for the polymerization of olefins. Although some catalytic activity was observed under the conditions employed, the degree of activity and the properties observed in the resulting polymer product were discouraging of a belief that such monocyclopentadienyl transition metal compound could be usefully employed for commercial polymerization processes.

A need still exists for discovering catalyst systems that permit the production of higher molecular weight polyolefins and desirably with a narrow molecular weight distribution. It is further desirable that a catalyst be discovered which, within reasonable ranges of ethylene to α-olefin monomer ratios, will catalyze the incorporation of higher contents of α-olefin comonomers in the production of ethylene-α-olefins copolymers.

SUMMARY OF THE INVENTION

The catalyst system of this invention comprises a transition metal component from Group IV B of the Periodic Table of the Elements (*CRC Handbook of Chemistry and Physics*, 68th ed. 1987–1988) and an alumoxane component which may be employed in solution, slurry or bulk phase polymerization procedure to produce a polyolefin of high weight average molecular weight and relatively narrow molecular weight distribution.

The "Group IV B transition metal component" of the catalyst system is represented by the formula:

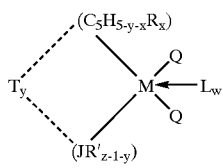

wherein: M is Zr, Hf or Ti in its highest formal oxidation state (+4, $d^0$ complex);

- $(C_2H_{5-y-x}R_x)$ is a cyclopentadienyl ring which is substituted with from zero to five substituent groups R, "x" is 0, 1, 2, 3, 4 or 5 denoting the degree of substitution, and each substituent group R is, independently, a radical selected from a group consisting of $C_1-C_{20}$ hydrocarbyl radicals, substituted $C_1-C_{20}$ hydrocarbyl radicals wherein one or more hydrogen atoms is replaced by a halogen radical, an amido radical, a phosphido radical, and alkoxy radical or any other radical containing a Lewis acidic or basic functionality; $C_1-C_{20}$ hydrocarbyl-substituted metalloid radicals wherein the metalloid is selected from the Group IV A of the Periodic Table of Elements; halogen radical, amido radicals, phosphido radicals, alkoxy radicals, alkylborido radicals or any other radical containing Lewis acidic or basic functionality; or $(C_2H_{5-y-x}R_x)$ is a cyclopentadienyl ring in which at least two adjacent R-groups are joined forming a $C_4-C_{20}$ ring to give a saturated or unsaturated polycyclic cyclopentadienyl ligand such as indenyl, tetrahydroindenyl, fluorenyl or octahydrofluorenyl;

- $(JR'_{z-1-y})$ is a heteroatom ligand in which J is an element with a coordination number of three from Group V A or an element with a coordination number of two from Group VI A of the Periodic Table of Elements, preferably nitrogen, phosphorus, oxygen or sulfur, and each R' is, independently a radical selected from a group consisting of $C_1-C_{20}$ hydrocarbyl radicals, substituted $C_1-C_{20}$ hydrocarbyl radicals wherein one or more hydrogen atoms are replaced by a halogen radical, an amido radical, a phosphido radical, an alkoxy radical or any other radical containing a Lewis acidic or basic functionality, and "z" is the coordination number of the element J;

- each Q may be independently any univalent anionic ligand such as a halide, hydride, or substituted or unsubstituted $C_1-C_{20}$ hydrocarbyl, alkoxide, aryloxide, amide, arylamide, phosphide or arylphosphide, provided that where any Q is a hydrocarbyl such Q is different from $(C_2H_{5-y-x}R_x)$, or both Q together may be an alkylidene or a cyclometallated hydrocarbyl or any other divalent anionic chelating ligand;

- "y" is 0 or 1 when w is greater than 0; y is 1 when w is 0; when "y" is 1, T is a covalent bridging group containing a Group IV A or V A element such as, but not limited to, a dialkyl, alkylaryl or diaryl silicon or germanium radical, alkyl or aryl phosphine or amine radical, or a hydrocarbyl radical such as methylene, ethylene and the like;

- L is a neutral Lewis base such as diethylether, tetraethylammonium chloride, tetrahydrofuran, dimethylaniline, aniline, trimethylphosphine, n-butylamine, and the like; and "w" is a number from 0 to 3. L can also be a second transition metal compound of the same type such that the two metal centers M and M' are bridged by Q and Q', wherein M' has the same meaning as M and Q' has the same meaning as Q. Such dimeric compounds are represented by the formula:

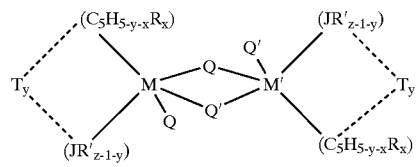

The alumoxane component of the catalyst may be represented by the formulas: $(R^3—Al—O)_m$; $R^4(R^5—Al—O)_m—AlR^6$ or mixtures thereof, wherein $R^3–R^6$ are, independently, a $C_1–C_5$ alkyl group or halide and "m" is an integer ranging from 1 to about 50 and preferably is from about 13 to about 25.

Catalyst systems of the invention may be prepared by placing the "Group IV B transition metal component" and the alumoxane component in common solution in a normally liquid alkane or aromatic solvent, which solvent is preferably suitable for use as a polymerization diluent for the liquid phase polymerization of an olefin monomer.

Those species of the Group IV B transition metal component wherein the metal is titanium have been found to impart beneficial properties to a catalyst system which are unexpected in view of what is known about the properties of bis(cyclopentadienyl) titanium compounds which are cocatalyzed by alumoxanes. Whereas titanocenes in their soluble form are generally unstable in the presence of aluminum alkyls, the monocyclopentadienyl titanium metal components of this invention, particularly those wherein the heteroatom is nitrogen, generally exhibit greater stability in the presence of aluminum alkyls, higher catalyst activity rates and higher α-olefin comonomer incorporation.

Further, the titanium species of the Group IV B transition metal component catalyst of this invention generally exhibit higher catalyst activities and the production of polymers of greater molecular weight and α-olefin comonomer contents than catalyst systems prepared with the zirconium or hafnium species of the Group IV B transition metal component.

A typical polymerization process of the invention such as for the polymerization or copolymerization of ethylene comprises the steps of contacting ethylene or $C_3–C_{20}$ α-olefins alone, or with other unsaturated monomers including $C_3–C_{20}$ α-olefins, $C_5–C_{20}$ diolefins, and/or acetylenically unsaturated monomers either alone or in combination with other olefins and/or other unsaturated monomers, with a catalyst comprising, in a suitable polymerization diluent, the Group IV B transition metal component illustrated above; and a methylalumoxane in an amount to provide a molar aluminum to transition metal ratio of from about 1:1 to about 20,000:1 or more; and reacting such monomer in the presence of such catalyst system at a temperature of from about −100° C. to about 300° C. for a time of from about 1 second to about 10 hours to produce a polyolefin having a weight average molecular weight of from about 1,000 or less to about 5,000,000 or more and a molecular weight distribution of from about 1.5 to about 15.0.

DESCRIPTION OF THE PREFERRED EMBODIMENT

Catalyst Component

The Group IV B transition metal component of the catalyst system is represented by the general formula:

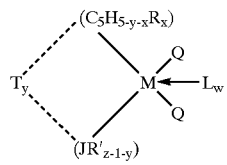

wherein M is Zr, Hf or Ti in its highest formal oxidation state (+4, $d^0$ complex);

($C_2H_{5-y-x}R_x$) is a cyclopentadienyl ring which is substituted with from zero to five substituent groups R, "x" is 0, 1, 2, 3, 4 or 5 denoting the degree of substitution, and each substituent group R is, independently, a radical selected from a group consisting of $C_1$–$C_{20}$ hydrocarbyl radicals, substituted $C_1$–$C_{20}$ hydrocarbyl radicals wherein one or more hydrogen atoms is replaced by a halogen radical, an amido radical, a phosphido radical, an alkoxy radical or any other radical containing a Lewis acidic or basic functionality, $C_1$–$C_{20}$ hydrocarbyl-substituted metalloid radicals wherein the metalloid is selected from the Group IV A of the Periodic Table of Elements; and halogen radicals, amido radicals, phosphido radicals, alkoxy radicals, alkylborido radicals or any other radical containing Lewis acidic or basic functionality; or ($C_2H_{5-y-x}R_x$) is a cyclopentadienyl ring in which two adjacent R-groups are joined forming $C_4$–$C_{20}$ ring to give a saturated or unsaturated polycyclic cyclopentadienyl ligand such as indenyl, tetrahydroindenyl, fluorenyl or octahydrofluorenyl;

($JR'_{z-1-y}$) is a heteroatom ligand in which J is an element with a coordination number of three from Group V A or an element with a coordination number of two from Group VI A of the Periodic Table of Elements, preferably nitrogen, phosphorus, oxygen or sulfur with nitrogen being preferred, and each R' is, independently a radical selected from a group consisting of $C_1$–$C_{20}$ hydrocarbyl radicals, substituted $C_1$–$C_{20}$ hydrocarbyl radicals wherein one or more hydrogen atoms is replaced by a halogen radical, an amido radical, a phosphido radical, and alkoxy radical or any other radical containing a Lewis acidic or basic functionality, and "z" is the coordination number of the element J;

each Q is, independently, any univalent anionic ligand such as a halide, hydride, or substituted or unsubstituted $C_1$–$C_{20}$ hydrocarbyl, alkoxide, aryloxide, amide, arylamide, phosphide or arylphosphide, provided that where any Q is a hydrocarbyl such Q is different from ($C_2H_{5-y-x}R_x$), or both Q together may be an alkylidene or a cyclometallated hydrocarbyl or any other divalent anionic chelating ligand;

"y" is 0 or 1 when w is greater than 0, and y is 1 when w equals 0; when "y" is 1, T is a covalent bridging group containing a Group IV A or V A element such as, but not limited to, a dialkyl, alkylaryl or diaryl silicon or germanium radical, alkyl or aryl phosphine or amine radical, or a hydrocarbyl radical such as methylene, ethylene and the like; and L is a neutral Lewis base such as diethylether, tetrahydrofuran, dimethylaniline, aniline, trimethylphosphine, n-butylamine, and the like; and "w" is a number from 0 to 3; L can also be a second transition metal compound of the same type such that the two metal centers M and M' are bridged by Q and Q', wherein M' has the same meaning as M and Q' has the same meaning as Q. Such compounds are represented by the formula:

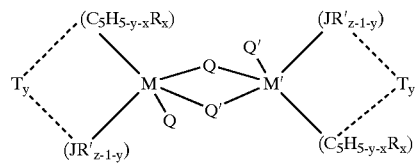

Examples of the T group which are suitable as a constituent group of the Group IV B transition metal component of the catalyst system are identified in column 1 of Table 1 under the heading "T".

Exemplary hydrocarbyl radicals for Q are methyl, ethyl, propyl, butyl, amyl, isoamyl, hexyl, isobutyl, heptyl, octyl, nonyl, decyl, cetyl, 2-ethylhexyl, phenyl and the like, with methyl being preferred. Exemplary halogen atoms for Q include chlorine, bromine, fluorine and iodine, with chlorine being preferred. Exemplary alkoxides and aryloxides for Q are methoxide, phenoxide and substituted phenoxides such as 4-methylphenoxide. Exemplary amides of Q are dimethylamide, diethylamide, methylethylamide, di-t-butylamide, diisoproylamide and the like. Exemplary aryl amides are diphenylamide and any other substituted phenyl amides. Exemplary phosphides of Q are diphenylphosphide, dicyclohexylphosphide, diethylphosphide, dimethylphosphide and the like. Exemplary alkyldiene radicals for both Q together are methylidene, ethylidene and propylidene. Examples of the Q group which are suitable as a constituent group or element of the Group IV B transition metal component of the catalyst system are identified in column 4 of Table 1 under the heading "Q".

Suitable hydrocarbyl and substituted hydrocarbyl radicals, which may be substituted as an R group for at least one hydrogen atom in the cyclopentadienyl ring, will contain from 1 to about 20 carbon atoms and include straight and branched alkyl radicals, cyclic hydrocarbon radicals, alkyl-substituted cyclic hydrocarbon radicals, aromatic radicals and alkyl-substituted aromatic radicals, amido-substituted hydrocarbon radicals, phosphido-substituted hydrocarbon radicals, alkoxy-substituted hydrocarbon radicals, and cyclopentadienyl rings containing one or more fused saturated or unsaturated rings. Suitable organometallic radicals, which may be substituted as an R group for at least one hydrogen atom in the cyclopentadienyl ring, include trimethylsilyl, triethylsilyl, ethyldimethylsilyl methyldiethylsilyl, triphenylgermyl, trimethylgermyl and the like. Other suitable radicals that may be substituted for one or more hydrogen atom in the cyclopentadienyl ring include halogen radicals, amido radicals, phosphido radicals, alkoxy radicals, alkyl boride radicals and the like. Examples of cyclopentadienyl ring groups ($C_2H_{5-y-x}R_x$) which are suitable as a constituent group of the Group IV B transition metal component of the catalyst system are identified in Column 2 of Table 1 under the heading ($C_2H_{5-y-x}R_x$).

Suitable hydrocarbyl and substituted hydrocarbyl radicals, which may be substituted as an R' group for at least one hydrogen atom in the heteroatom J ligand group, will contain from 1 to about 20 carbon atoms and include straight and branched alkyl radicals, cyclic hydrocarbon radicals, alkyl-substituted cyclic hydrocarbon radicals, aromatic radicals, alkyl-substituted aromatic radicals, halogen radicals, amido radicals, phosphido radicals and the like. Examples of heteroatom ligand groups ($JR'_{z-1-y}$) which are suitable as a constituent group of the Group IV B transition metal component of the catalyst system are identified in column 3 of Table 1 under the heading ($JR'_{z-1-y}$).

Table 1 depicts representative constituent moieties for the "Group IV B transition metal component", the list is for illustrative purposes only and should not be construed to be limiting in any way. A number of final components may be formed by permuting all possible combinations of the constituent moieties with each other. Illustrative compounds are: dimethylsilyltetramethylcyclopentadienyl-tert-butylamido zirconium dichloride, dimethylsilyltetramethylcyclopentadienyl-tert-butylamido hafnium dichloride, dimethylsilyl-tert-butylcyclopentadienyl-tert-butylamido zirconium dichloride, dimethylsilyl-tert-butylcyclopentadienyl-tert-butylamido hafnium dichloride, dimethylsilyltrimethylsilylcyclopentadienyl-tert-butylamido zirconium dichloride, dimethylsilyltetramethylcyclopentadienylphenylamido zirconium dichloride, dimethylsilyltetramethylcyclopentadienylphenylamido hafnium dichloride, methylphenylsilyltetramethylcyclopentadienyl-tert-butylamido zirconium dichloride, methylphenylsilyltetramethylcyclopentadienyl-tert-butylamido hafnium dichloride, methylphenylsilyltetramethylcyclopentadienyl-t-butylamido hafnium dimethyl, dimethylsilyltetramethylcyclopentadienyl-p-n-butylphenylamido zirconium dichloride, dimethylsilyltetramethylcyclopentadienyl-p-n-butylphenylamido hafnium dichloride.

As noted, titanium species of the Group IV B transition metal compound have generally been found to yield catalyst systems which in comparison to their zirconium or hafnium analogus, are of higher activity and α-olefin comonomer incorporating ability. Illustrative, but not limiting of the titanium species which exhibit such superior properties are methylphenylsilyltetramethylcyclopentadienyl-tert-butylamido titanium dichloride, dimethylsilyltetramethylcyclopentadienyl-p-n-butylphenylamido titanium dichloride, dimethylsilyltetramethylcyclopentadienyl-p-methoxyphenylamido titanium dichloride, dimethylsilyl-tert-butylcyclopentadienyl-2,5-di-tert-butylphenylamido titanium dichloride, dimethylsilylindenyl-tert-butylamido titanium dichloride, dimethylsilyltetramethylcyclopentadienylcyclohexylamido titanium dichloride, dimethylsilylfluorenylcyclohexylamido titanium dichloride, dimethylsilyltetramethylcyclopentadienylphenylamido titanium dichloride, dimethylsilyltetramethylcyclopentadienyl-tert-butylamido titanium dichloride, dimethylsilyltetramethylcyclopentadienylcyclododecylamido titanium dichloride, and the like.

For illustrative purposes, the above compounds and those permuted from Table 1 do not include the neutral Lewis base ligand (L). The conditions under which complexes containing neutral Lewis base ligands such as ether or those which form dimeric compounds is determined by the steric bulk of the ligands about the metal center. For example, the t-butyl group in $Me_2Si(Me_4C_5)(N\text{-}t\text{-}Bu)ZrCl_2$ has greater steric requirements than the phenyl group in $Me_2Si(Me_4C_5)(NPh)ZrCl_2.Et_2O$ thereby not permitting ether coordination in the former compound. Similarly, due to the decreased steric bulk of the trimethylsilylcyclopentadienyl group in $[Me_2Si(Me_3SiC_5H_3)(N\text{-}t\text{-}Bu)ZrCl_2]_2$ versus that of the tetramethylcyclopentadienyl group in $Me_2Si(Me_4C_5)(N\text{-}t\text{-}Bu)ZrCl_2$, the former compound is dimeric and the latter is not.

TABLE 1

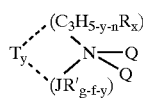

| T (when y-1) | $(C_3R_{5-y-n}R_x)$ | $(JR'_{g-f-y})$ | Q | H |
|---|---|---|---|---|
| dimethylsilyl | cyclopentadienyl | α-butylamido | hydride | siroonium |
| diethylsilyl | methylcyclopentadienyl | phenylamido | chloro | hafnium |
| di-n-propylsilyl | 1,2-dimethylcyclopentadienyl | p-n-butylphenylamido | methyl | titanium |
| diisopropylsilyl | 1,3-dimethylcyclopentadienyl | cyclohexylamido | ethyl | |
| di-n-butylsilyl | indenyl | perflurophenylamido | phenyl | |
| di-t-butylsilyl | 1,2-diethylcyclopentadienyl | n-butylamido | fluoro | |
| di-n-hexylsilyl | tetramethylcyclopentadienyl | methylamido | bromo | |
| methylphenylsilyl | ethylcyclopentadienyl | ethylamido | iodo | |
| ethylmethylsilyl | n-butylcyclopentadienyl | n-propylamido | n-propyl | |
| diphenylsilyl | cyclohexylmethylcyclopentadienyl | isopropylamido | isopropyl | |
| di(p-t-butylphenethylsilyl) | n-octylcyclopentadienyl | benzylamido | n-butyl | |
| β-hexylmethylsilyl | β-phenylpropylcyclopentadienyl | t-butylphosphido | amyl | |
| cyclopentamethylenesilyl | tetrahydroindenyl | ethylphosphido | isoamyl | |
| cyclotetramethylenesilyl | propylcyclopentadienyl | phenylphosphido | hexyl | |
| cyclotrimethylenesilyl | t-butylcyclopentadienyl | cyclohexylphosphido | isobutyl | |
| dimethylgermanyl | benzylcyclopentadienyl | oxo (when y = 1) | heptyl | |
| diethylgermanyl | diphenylmethylcyclopentadienyl | sulfido (when y = 1) | octyl | |
| phenylamido | trimethylgermylcyclopentadienyl | methoxide (when y = 0) | nonyl | |
| t-butylamido | trimethylstannylcyclopentadienyl | ethoxide (when y = 0) | decyl | |
| methylamido | triethylplumbylcyclopentadienyl | methylthio (when y = 0) | cetyl | |

TABLE 1-continued $$T_y \overset{(C_3H_{5-y-n}R_x)}{\underset{(JR'_{g-f-y})}{\diagdown}} N - Q$$

| T (when y-1) | $(C_3R_{5-y-n}R_x)$ | $(JR'_{g-f-y})$ | Q | H |
|---|---|---|---|---|
| t-butylphosphido | trifluromethylcyclopentadienyl | ethylthio (when y = 0) | methoxy | |
| ethylphosphido | trimethylsilylcyclopentadienyl | | ethoxy | |
| phenylphosphido | pentamethylcycloopentadienyl (when y = 0) | | propoxy | |
| dimethylmethylene | octahydrofluoronyl | | phenoxy | |
| diethylmethylene | N,N-dimethylamidocyclopentadienyl | | dimethylamido | |
| ethylene | dimethylphosphidocyclopentadienyl | | diethylamido | |
| dimethylethylene | methoxycyclopentadienyl | | methylethylamido | |
| diethylethylene | dimethylboridocyclopentadienyl | | di-t-butylamido | |
| dipropylethylene | (N,N-dimethylamidomethyl)cyclopentadienyl | | diphenylamido | |
| propylene | | | diphenylphosphido | |
| dimethylpropylene | | | dicyclohexylphosphido | |
| diethylpropylene | | | dimethylphosphido | |
| 1,1-dimethyl-3,3-dimethyl-propylene | | | methylidene (both Q) | |
| tetramethyldisiloxane | | | ethylidene (both Q) | |
| 1,1,4,4-tetramethylidisilylethylene | | | propylidene (both Q) | |
| | | | ethyleneglycoldianion (both Q) | |

Generally the bridged species of the Group IV B transition metal compound ("y"=1) are preferred. These compounds can be prepared by reacting a cyclopentadienyl lithium compound with a dihalo compound whereupon a lithium halide salt is liberated and a monohalo substituent becomes covalently bound to the cyclopentadienyl compound. The so substituted cyclopentadienyl reaction product is next reacted with a lithium salt of a phosphide, oxide, sulfide or amide (for the sake of illustrative purposes, a lithium amide) whereupon the halo element of the monohalo substituent group of the reaction product reacts to liberate a lithium halide salt and the amine moiety of the lithium amide salt becomes covalently bound to the substituent of the cyclopentadienyl reaction product. The resulting amine derivative of the cyclopentadienyl product is then reacted with a alkyl lithium reagent whereupon the labile hydrogen atoms, at the carbon atom of the cyclopentadienyl compound and at the nitrogen atom of the amine moiety covalently bound to the substituent group, react with the alkyl of the lithium alkyl reagent to liberate the alkane and produce a dilithium salt of the cyclopentadienyl compound. Thereafter the bridged species of the Group IV B transition metal compound is produced by reacting the dilithium salt cyclopentadienyl compound with a Group IV B transition metal preferably a Group IV B transition metal halide.

Unbridged species of the Group IV B transition metal compound can be prepared from the reaction of a cyclopentadienyl lithium compound and a lithium salt of an amine with a Group IV B transition metal halide.

Suitable, but not limiting, Group IV B transition metal compounds which may be utilized in the catalyst system of this invention include those bridged species ("y"=1) wherein the T group bridge is a dialkyl, diaryl or alkylaryl silane, or methylene or ethylene. Exemplary of the more preferred species of bridged Group IV B transition metal compounds are dimethylsilyl, methylphenylsilyl, diethylsilyl, ethylphenylsilyl, diphenylsilyl, ethylene or methylene bridged compounds. Most preferred of the bridged species are dimethylsilyl, diethylsilyl and methylphenylsilyl bridged compounds.

Suitable Group IV B transition metal compounds which are illustrative of the unbridged ("y"=0) species which may be utilized in the catalyst systems of this invention are exemplified by pentamethylcyclopentadienyldi-t-butylphosphinodimethyl hafnium; pentamethylcyclopentadienyldi-t-butylphosphinomethylethyl hafnium; cyclopentadienyl-2-methylbutoxide dimethyl titanium.

To illustrate members of the Group IV B transition metal component, select any combination of the species in Table 1. An example of a bridged species would be dimethylsilyclopentadienyl-t-butylamidodichloro zirconium; an example of an unbridged species would be cyclopentadienyldi-t-butylamidodichloro zirconium.

Generally, wherein it is desired to produce an α-olefin copolymer which incorporates a high content of α-olefin, the species of Group IV B transition metal compound preferred is one of titanium. The most preferred species of titanium metal compounds are represented by the formula:

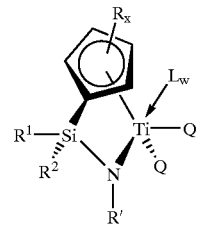

wherein Q, L, R', R, "x" and "w" are as previously defined and $R^1$ and $R^2$ are each independently a $C_1$ to $C_{20}$ hydrocarbyl radicals, substituted $C_1$ to $C_{20}$ hydrocarbyl radicals wherein one or more hydrogen atom is replaced by a halogen atom; $R^1$ and $R^2$ may also be joined forming a $C_3$ to $C_{20}$ ring which incorporates the silicon bridge.

The alumoxane component of the catalyst system is an oligomeric compound which may be represented by the general formula $(R^3—Al—O)$, which is a cyclic compound, or may be $R^4(R^5—Al—O—)_m—AlR^6{}_2$ which is a linear compound. An alumoxane is generally a mixture of both the linear and cyclic compounds. In the general alumoxane formula $R^3$, $R^4$, $R^5$ and $R^6$ are, independently a $C_1$–$C_5$ alkyl radical, for example, methyl, ethyl, propyl, butyl or pentyl and "m" is an integer from 1 to about 50. Most preferably, $R^3$, $R^4$, $R^5$ and $R^6$ are each methyl and "m" is at least 4. When an alkyl aluminum halide is employed in the preparation of the alumoxane, one or more $R^{3-6}$ groups may be halide.

As is now well known, alumoxanes can be prepared by various procedures. For example, a trialkyl aluminum may be reacted with water, in the form of a moist inert organic solvent; or the trialkyl aluminum may be contacted with a hydrated salt, such as hydrated copper sulfate suspended in an inert organic solvent, to yield an alumoxane. Generally, however prepared, the reaction of a trialkyl aluminum with a limited amount of water yields a mixture of both linear and cyclic species of alumoxane.

Suitable alumoxanes which may be utilized in the catalyst systems of this invention are those prepared by the hydrolysis of a trialkylaluminum; such as trimethylaluminum, triethyaluminum, tripropylaluminum; triisobutylaluminum, dimethylaluminumchloride, diisobutylaluminumchloride, diethylaluminumchloride, and the like. The most preferred alumoxane for use is methylalumoxane (MAO). Methylalumoxanes having an average degree of oligomerization of from about 4 to about 25 ("m"=4 to 25), with a range of 13 to 25, are the most preferred.

Catalyst Systems

The catalyst systems employed in the method of the invention comprise a complex formed upon admixture of the Group IV B transition metal component with an alumoxane component. The catalyst system may be prepared by addition of the requisite Group IV B transition metal and alumoxane components to an inert solvent in which olefin polymerization can be carried out by a solution, slurry or bulk phase polymerization procedure.

The catalyst system may be conveniently prepared by placing the selected Group IV B transition metal component and the selected alumoxane component, in any order of addition, in an alkane or aromatic hydrocarbon solvent—preferably one which is also suitable for service as a polymerization diluent. Where the hydrocarbon solvent utilized is also suitable for use as a polymerization diluent, the catalyst system may be prepared in situ in the polymerization reactor. Alternatively, the catalyst system may be separately prepared, in concentrated form, and added to the polymerization diluent in a reactor. Or, if desired, the components of the catalyst system may be prepared as separate solutions and added to the polymerization diluent in a reactor, in appropriate ratios, as is suitable for a continuous liquid phase polymerization reaction procedure. Alkane and aromatic hydrocarbons suitable as solvents for formation of the catalyst system and also as a polymerization diluent are exemplified by, but are not necessarily limited to, straight and branched chain hydrocarbons such as isobutane, butane, pentane, hexane, heptane, octane and the like, cyclic and alicyclic hydrocarbons such as cyclohexane, cycloheptane, methylcyclohexane, methylcycloheptane and the like, and aromatic and alkyl-substituted aromatic compounds such as benzene, toluene, xylene and the like. Suitable solvents also include liquid olefins which may act as monomers or comonomers including ethylene, propylene, 1-butene, 1-hexene and the like.

In accordance with this invention optimum results are generally obtained wherein the Group IV B transition metal compound is present in the polymerization diluent in a concentration of from about 0.0001 to about 1.0 millimoles/liter of diluent and the alumoxane component is present in an amount to provide a molar aluminum to transition metal ratio of from about 1:1 to about 20,000:1. Sufficient solvent should be employed so as to provide adequate heat transfer away from the catalyst components during reaction and to permit good mixing.

The catalyst system ingredients—that is, the Group IV B transition metal, the alumoxane, and polymerization diluent—can be added to the reaction vessel rapidly or slowly. The temperature maintained during the contact of the catalyst components can vary widely, such as, for example, from −10° to 300° C. Greater or lesser temperatures can also be employed. Preferably, during formation of the catalyst system, the reaction is maintained within a temperature of from about 25° to 100° C., most preferably about 25° C.

At all times, the individual catalyst system components, as well as the catalyst system once formed, are protected from oxygen and moisture. Therefore, the reactions to prepare the catalyst system are performed in an oxygen and moisture free atmosphere and, where the catalyst system is recovered separately it is recovered in an oxygen and moisture free atmosphere. Preferably, therefore, the reactions are performed in the presence of an inert dry gas such as, for example, helium or nitrogen.

Polymerization Process

In a preferred embodiment of the process of this invention the catalyst system is utilized in the liquid phase (slurry, solution, suspension or bulk phase or combination thereof), high pressure fluid phase or gas phase polymerization of an olefin monomer. These processes may be employed singularly or in series. The liquid phase process comprises the steps of contacting an olefin monomer with the catalyst system in a suitable polymerization diluent and reacting said monomer in the presence of said catalyst system for a time and at a temperature sufficient to produce a polyolefin of high molecular weight.

The monomer for such process may comprise ethylene alone, for the production of a homopolyethylene, or ethylene in combination with an $\alpha$-olefin having 3 to 20 carbon atoms for the production of an ethylene-$\alpha$-olefin copolymer. Homopolymers of higher $\alpha$-olefin such as propylene, butene, styrene and copolymers thereof with ethylene and/or $C_4$ or higher $\alpha$-olefins and diolefins can also be prepared. Conditions most preferred for the homo- or copolymerization of ethylene are those wherein ethylene is submitted to the reaction zone at pressures of from about 0.019 psia to about 50,000 psia and the reaction temperature is maintained at from about −100° to about 300° C. The aluminum to transition metal molar ratio is preferably from about 1:1 to 18,000 to 1. A more preferable range would be 1:1 to 2000:1. The reaction time is preferably from about 10 seconds to about 1 hour. Without limiting in any way the scope of the invention, one means for carrying out the process of the present invention for production of a copolymer is as follows: in a stirred-tank reactor liquid $\alpha$-olefin monomer is introduced, such as 1-butene. The catalyst system is introduced via nozzles in either the vapor or liquid phase. Feed ethylene gas is introduced either into the vapor phase of the reactor, or sparged into the liquid phase as is well known in the art. The reactor contains a liquid phase composed substantially of liquid $\alpha$-olefin comonomer, together with dissolved ethylene gas, and a vapor phase containing vapors of all monomers. The reactor temperature and pressure may be controlled via reflux of vaporizing $\alpha$-olefin monomer (autorefrigeration), as well as by cooling coils, jackets etc. The polymerization rate is controlled by the concentration of catalyst. The ethylene content of the polymer product is determined by the ratio of ethylene to α-olefin comonomer in the reactor, which is controlled by manipulating the relative feed rates of these components to the reactor.

As before noted, a catalyst system wherein the Group IV B transition metal component is a titanium species has the ability to incorporate high contents of α-olefin comonomers. Accordingly, the selection of the Group IV B transition metal component is another parameter which may be utlized as a control over the ethylene content of a copolymer within a reasonable ratio of ethylene to α-olefin comonomer.

EXAMPLES

In the examples which illustrate the practice of the invention the analytical techniques described below were employed for the analysis of the resulting polyolefin products. Molecular weight determinations for polyolefin products were made by Gel Permeation Chromatography (GPC) according to the following technique. Molecular weights and molecular weight distributions were measured using a Waters 150 gel permeation chromatograph equipped with a differential refractive index (DRI) detector and a Chromatix KMX-6 on-line light scattering photometer. The system was used at 135° C. with 1,2,4-trichlorobenzene as the mobile phase. Shodex (Showa Denko America, Inc.) polystyrene gel columns 802, 803, 804 and 805 were used. This technique is discussed in "Liquid Chromatography of Polymers and Related Materials III", J. Cazes editor, Marcel Dekker. 1981, p. 207, which is incorporated herein by reference. No corrections for column spreading were employed; however, data on generally accepted standards, e.g. National Bureau of Standards Polyethylene 1484 and anionically produced hydrogenated polyisoprenes (an alternating ethylene-propylene copolymer) demonstrated that such corrections on Mw/Mn (=MWD) were less than 0.05 units. Mw/Mn was calculated from elution times. The numerical analyses were performed using the commercially available Beckman/CIS customized LALLS software in conjunction with the standard Gel Permeation package, run on a HP 1000 computer.

The following examples are intended to illustrate specific embodiments of the invention and are not intended to limit the scope of the invention.

All procedures were performed under an inert atmosphere of helium or nitrogen. Solvent choices are often optional, for example, in most cases either pentane or 30-60 petroleum ether can be interchanged. The lithiated amides were prepared from the corresponding amines and either n-BuLi or MeLi. Published methods for preparing $LiHC_5Me_4$ include C. M. Fendrick et al. *Organometallics*, 3, 819 (1984) and F. H. Köhler and K. H. Doll, *Z. Naturforich*, 376, 144 (1982). Other lithiated substituted cyclopentadienyl compounds are typically prepared from the corresponding cyclopentadienyl ligand and n-BuLi or MeLi, or by reaction of MeLi with the proper fulvene. $TiCl_4$, $ZrCl_4$ and $HfCl_4$ were purchased from either Aldrich Chemical Company or Cerac. $TiCl_4$ was typically used in its etherate form. The etherate, $TiCl_4 \cdot 2Et_2O$, can be prepared by gingerly adding $TiCl_4$ to diethylether. Amines, silanes and lithium reagents were purchased from Aldrich Chemical Company or Petrarch Systems. Methylalumoxane was supplied by either Sherring or Ethyl Corp.

Examples A–L and AT–IT of Group IV B Transition Metal-Components

Example A

Compound A: Part 1. $Me_4HC_5Li$ (10.0 g, 0.078 mol) was slowly added to a $Me_2SiCl_2$ (11.5 ml, 0.095 mol, in 225 ml of tetrahydrofuran (thf) solution). The solution was stirred for 1 hour to assure complete reaction. The thf solvent was then removed via a vacuum to a cold trap held at −196° C. Pentane was added to precipitate out the LiCl. The mixture was filtered through Celite. The solvent was removed from the filtrate. $Me_4HC_5SiMe_2Cl$ (15.34 g, 0.071 mol) was recovered as a pale yellow liquid.

Part 2. $Me_4HC_5SiMe_2Cl$ (10.0 g, 0.047 mol) was slowly added to a suspension of LiHN-t-Bu (3.68 g, 0.047 mol, ~100 ml thf). The mixture was stirred overnight. The thf was then removed via a vacuum to a cold trap held at −196° C. Petroleum ether (~100 ml) was added to precipitate out the LiCl. The mixture was filtered through Celite. The solvent was removed from the filtrate. $Me_2Si(Me_4HC_5)(HN-t-Bu)$ (11.14 g. 0.044 mol) was isolated as a pale yellow liquid.

Part 3. $Me_2Si(Me_4HC_5)(HN-t-Bu)$ (11.14 g, 0.044 mol) was diluted with ~100 ml $Et_2O$. MeLi (1.4 M, 64 ml, 0.090 mol) was slowly added. The mixture was allowed to stir for ½ hour after the final addition of MeLi. The ether was reduced in volume prior to filtering off the product. The product, $[Me_2Si(Me_4C_5)(N-t-Bu)]Li_2$, was washed with several small portions of ether, then vacuum dried.

Part 4. $[Me_2Si(Me_4C_5)(N-t-Bu)]Li_2$ (3.0 g, 0.011 mol) was suspended in ~150 ml $Et_2O$. $ZrCl_4$ (2.65 g, 0.011 mol) was slowly added and the resulting mixture was allowed to stir overnight. The ether was removed via a vacuum to a cold trap held at −196° C. Pentane was added to precipitate out the LiCl. The mixture was filtered through Celite twice. The pentane was significantly reduced in volume and the pale yellow solid was filtered off and washed with solvent. $Me_2Si(Me_4C_5)(N-t-Bu)ZrCl_2$ (1.07 g, 0.0026 mole) was recovered. Additional $Me_2Si(Me_4C_5)(N-t-Bu)ZrCl_2$ was recovered from the filtrate by repeating the recrystallization procedure. Total yield, 1.94 g, 0.0047 mol.

Example B

Compound B: The same procedure of Example A for preparing compound A was followed with the exception of the use of $HfCl_4$ in place of $ZrCl_4$ in Part 4. Thus, when $[Me_2Si(Me_4C_5)(N-t-Bu)]Li_2$ (2.13 g, 0.0081 mol) and $HfCl_4$ (2.59 g, 0.0081 mol) were used, $Me_2Si(Me_4C_5)(N-t-Bu)HfCl_2$ (0.98 g, 0.0020 mol) was produced.

Example C

Compound C: Part 1. $Me_2SiCl_2$ (7.5 ml, 0.062 mol) was diluted with ~30 ml thf. A $t-BuH_4C_5Li$ solution (7.29 g, 0.056 mol, ~100 ml thf) was slowly added, and the resulting mixture was allowed to stir overnight. The thf was removed via a vacuum to a trap held at −196° C. Pentane was added to precipitate out the LiCl, and the mixture was filtered through Celite. The pentane was removed from the filtrate leaving behind a pale yellow liquid, $t-BuH_4C_5SiMe_2Cl$ (10.4 g, 0.048 mol).

Part 2. To a thf solution of LiHN-t-Bu (3.83 g, 0.048 mol, ~125 ml), $t-BuH_4C_5SiMe_2Cl$ (10.4 g, 0.048 mol) was added drop wise. The resulting solution was allowed to stir overnight. The thf was removed via a vacuum to a trap held at −196° C. Pentane was added to precipitate out the LiCl, and the mixture was filtered through Celite. The pentane was removed from the filtrate leaving behind a pale yellow liquid, $Me_2Si(t-BuH_4C_5)(NH-t-Bu)$ (11.4 g, 0.045 mol).

Part 3. $Me_2Si(t-BuH_4C_5)(NH-t-Bu)$ (11.4 g, 0.045 mol) was diluted with ~100 ml $Et_2O$. MeLi (1.4 M, 70 ml, 0.098 mol) was slowly added. The mixture was allowed to stir overnight. The ether was removed via a vacuum to a trap held at −196° C., leaving behind a pale yellow solid, [He$_2$Si(t-BuH$_3$C$_5$)(N-t-Bu)]Li$_2$ (11.9 g, 0.045 mol).

Part 4. [Me$_2$Si(t-BuH$_3$C$_5$)(N-t-Bu)]Li$_2$ (3.39 g 0.013 mol) was suspended in ~100 ml Et$_2$O. ZrCl$_4$ (3.0 g, 0.013 mol) was slowly added. The mixture was allowed to stir overnight. The ether was removed and pentane was added to precipitate out the LiCl. The mixture was filtered through Celite. The pentane solution was reduced in volume, and the pale tan solid was filtered off and washed several times with small quantities of pentane. The product of empirical formula Me$_2$Si(t-BuH$_3$C$_5$)(N-t-Bu)ZrCl$_2$ (2.43 g, 0.0059 mol) was isolated.

Example D

Compound D: The same procedure of Example C for preparing compound C was followed with the exception of the use of HfCl$_4$ in Part 4. Thus, when [Me$_2$Si(t-BuH$_3$C$_5$)(N-t-Bu)]Li$_2$ (3.29 g, 0.012 mol) and HfCl$_4$ (4.0 g, 0.012 mol) were used, the product of the empirical formula Me$_2$Si(t-BuH$_3$C$_5$)(N-t-Bu)HfCl$_2$ (1.86 g, 0.0037 mol) was produced.

Example E

Compound E: Part 1. Me$_2$SiCl$_2$ (7.0 g. 0.054 mol) was diluted with ~100 ml of ether. Me$_3$SiC$_5$H$_4$Li (5.9 g, 0.041 mol) was slowly added. Approximately 75 ml of thf was added and the mixture was allowed to stir overnight. The solvent was removed via a vacuum to a cold trap held at −196° C. Pentane was added to precipitate out the LiCl. The mixture was filtered through Celite. The solvent was removed from the filtrate giving Me$_2$Si(Me$_3$SiC$_5$H$_4$)Cl (8.1 g, 0.035 mol) as a pale yellow liquid.

Part 2. Me$_2$Si(Me$_3$SiC$_5$H$_4$)Cl (3.96 g. 0.017 mol) was diluted with ~50 ml of ether. LiHN-t-Bu (1.36 g, 0.017 mol) was slowly added, and the mixture was allowed to stir overnight. The ether was removed via a vacuum and pentane was added to precipitate the LiCl. The mixture was filtered through Celite, and the pentane was removed from the filtrate. Me$_2$Si(Me$_3$SiC$_5$H$_4$)(NH-t-Bu) (3.7 g, 0.014 mol) was isolated as a pale yellow liquid.

Part 3. Me$_2$Si(M$_3$SiC$_5$H$_4$)(NH-t-Bu) (3.7 g, 0.014 mol) as diluted with ether. MeLi (25 ml, 1.4 M in ether, 0.035 mol) was slowly added. The mixture was allowed to stir for 1.5 hours after the final addition of MeLi. The ether was removed via vacuum producing 4.6 g of a white solid formulated as Li$_2$[Me$_2$Si(Me$_3$SiC$_5$H$_3$)(N-t-Bu)].3/4Et$_2$O and unreacted MeLi which was not removed from the solid.

Part 4. Li$_2$[Me$_2$Si(Me$_3$SiC$_5$H$_3$)(N-t-Bu)].3/4Et$_2$O (1.44 g, 0.0043 mol) was suspended in ~50 ml of ether. ZrCl$_4$ (1.0 g, 0.0043 mol) was slowly added and the reaction was allowed to stir for a few hours. The solvent was removed via vacuum and pentane was added to precipitate the LiCl. The mixture was filtered through Celite, and the filtrate was reduced in volume. The flask was placed in the freezer (−40° C.) to maximize precipitation of the product. The solid was filtered off giving 0.273 g of an off white solid. The filtrate was again reduced in volume, the precipitate filtered off to give an additional 0.345 g for a total of 0.62 g of the compound with empirical formula Me$_2$Si(Me$_3$SiC$_5$H$_3$)(N-t-Bu)ZrCl$_2$. The x-ray crystal structure of this product reveals that the compound is dimeric in nature.

Example F

Compound F: Part 1. Me$_4$HC$_5$SiMe$_2$Cl was prepared as described in Example A for the preparation of compound A, Part 1.

Part 2. LiHNPh (4.6 g, 0.0462 mol) was dissolved in ~100 ml of thf. Me$_4$HC$_5$SiMe$_2$Cl (10.0 g. 0.0466 mol) was slowly added. The mixture was allowed to stir overnight. The thf was removed via a vacuum. Petroleum ether and toluene were added to precipitate the LiCl, and the mixture was filtered through Celite. The solvent was removed, leaving behind a dark yellow liquid, Me$_2$Si(Me$_4$HC$_5$)(NHPh) (10.5 g, 0.0387 mol).

Part 3. Me$_2$Si(Me$_4$HC$_5$)(NHPh) (10.5 g, 0.0387 mol) was diluted with ~60 ml of ether. MeLi (1.4 M in ether, 56 ml, 0.0784 mol) was slowly added and the reaction was allowed to stir overnight. The resulting white solid, Li$_2$[Me$_2$Si(Me$_4$C$_5$)(NPh).3/4Et$_2$O (11.0 g), was filtered off and was washed with ether.

Part 4. Li$_2$[Me$_2$Si(Me$_4$C$_5$)(NPh).3/4Et$_2$O (2.81 g, 0.083 mol) was suspended in ~40 ml of ether. ZrCl$_4$ (1.92 g. 0.0082 mol) was slowly added and the mixture was allowed to stir overnight. The ether was removed via a vacuum, and a mixture of petroleum ether and toluene was added to precipitate the LiCl. The mixture was filtered through Celite, the solvent mixture was removed via vacuum, and pentane was added. The mixture was placed in the freezer at −40° C. to maximize the precipitation of the product. The solid was then filtered off and washed with pentane. Me$_2$Si(Me$_4$C$_5$)(NPh)ZrCl$_2$.Et$_2$O was recovered as a pale yellow solid (1.89 g).

Example G

Compound G: The same procedure of Example F for preparing compound F was followed with the exception of the use of HfCl$_4$ in place of ZrCl$_4$ in Part 4. Thus, when Li$_2$[Me$_2$Si(Me$_4$C$_5$)(NPh)].3/4Et$_2$O (2.0 g, 0.0059 mol) and HfCl$_4$ (1.89 g, 0.0059 mol) were used, Me$_2$Si(Me$_4$C$_5$)(NPh)HfCl$_2$.1/2Et$_2$O (1.70 g) was produced.

Example H

Compound H: Part 1. MePhSiCl$_2$ (14.9 g, 0.078 mol) was diluted with ~250 ml of thf. Me$_4$C$_5$HLi (10.0 g. 0.078 mol) was slowly added as a solid. The reaction solution was allowed to stir overnight. The solvent was removed via a vacuum to a cold trap held at −196° C. Petroleum ether was added to precipitate out the LiCl. The mixture was filtered through Celite, and the pentane was removed from the filtrate. MePhSi(Me$_4$C$_5$H)Cl (20.8 g, 0.075 mol) was isolated as a yellow viscous liquid.

Part 2. LiHN-t-Bu (4.28 g, 0.054 mol) was dissolved in ~100 ml of thf. MePhSi(Me$_4$C$_5$H)Cl (15.0 g, 0.054 mol) was added drop wise. The yellow solution was allowed to stir overnight. The solvent was removed via vacuum. Petroleum ether was added to precipitate out the LiCl. The mixture was filtered through Celite, and the filtrate was evaporated down. MePhSi(Me$_4$C$_5$H)(NH-t-Bu) (16.6 g, 0.053 mol) was recovered as an extremely viscous liquid.

Part 3. MePhSi(Me$_4$C$_5$H)(NH-t-Bu) (16.6 g, 0.053 mol) was diluted with ~100 ml of ether. MeLi (76 ml, 0.106 mol, 1.4 M) was slowly added and the reaction mixture was allowed to stir for ~3 hours. The ether was reduced in volume and the lithium salt was filtered off and washed with pentane producing 20.0 g of a pale yellow solid formulated as Li$_2$[MePhSi(Me$_4$C$_5$)(N-t-Bu)].3/4Et$_2$O.

Part 4. Li$_2$[MePhSi(Me$_4$C$_5$)(N-t-Bu)].3/4Et$_2$O (5.0 g, 0.0131 mol) was suspended in ~100 ml of Et$_2$O. ZrCl$_4$ (3.06 g, 0.0131 mol) was slowly added. The reaction mixture was allowed to stir at room temperature for ~1.5 hours over which time the reaction mixture slightly darkened in color.

The solvent was removed via vacuum and a mixture of petroleum ether and toluene was added. The mixture was filtered through Celite to remove the LiCl. The filtrate was evaporated down to near dryness and filtered off. The off white solid was washed with petroleum ether. The yield of product, MePhSi(Me$_4$C$_5$)(N-t-Bu)ZrCl$_2$, was 3.82 g (0.0081 mol).

Example I

Compound I: Li$_2$[MePhSi(Me$_4$C$_5$)(N-t-Bu)].3/4Et$_2$O was prepared as described in Example H for the preparation of compound H, Part 3.

Part 4. Li$_2$(MePhSi(Me$_4$C$_5$)(N-t-Bu)].3/4Et$_2$O (5.00 g, 0.0131 mol) was suspended in ~100 ml of Et$_2$O. HfCl$_4$ (4.20 g, 0.0131 mol) was slowly added and the reaction mixture was allowed to stir overnight. The solvent was removed via vacuum and petroleum ether was added to precipitate out the LiCl. The mixture was filtered through Celite. The filtrate was evaporated down to near dryness and filtered off. The off white solid was washed with petroleum ether. MePhSi(Me$_4$C$_5$)(N-t-Bu)HfCl$_2$ was recovered (3.54 g, 0.0058 mole).

Example J

Compound J: MePhSi(Me$_4$C$_5$)(N-t-Bu)HfMe$_2$ was prepared by adding a stoichiometric amount of MeLi (1.4 M in ether) to MePhSi(Me$_4$C$_5$)(N-t-Bu)HfCl$_2$ suspended in ether. The white solid could be isolated in near quantitative yield.

Example K

Compound K: Part 1. Me$_4$C$_5$SiMe$_2$Cl was prepared as described in Example A for the preparation of compound A, Part 1.

Part 2. Me$_4$C$_5$SiMe$_2$Cl (10.0 g, 0.047 mol) was diluted with ~25 ml Et$_2$O. LiHNC$_5$H$_4$-p-n-Bu.1/10Et$_2$O (7.57 g, 0.047 mol) was added slowly. The mixture was allowed to stir for ~3 hours. The solvent was removed via vacuum. Petroleum ether was added to precipitate out the LiCl, and the mixture was filtered through Celite. The solvent was removed leaving behind an orange viscous liquid, Me$_2$Si(Me$_4$C$_5$H)(HNC$_6$H$_4$-p-n-Bu) (12.7 g, 0.039 mol).

Part 3. Me$_2$Si(Me$_4$C$_5$H)(HNC$_6$H$_4$-p-n-Bu) (12.7 g. 0.039 mol) was diluted with ~50 ml of Et$_2$O. MeLi (1.4 M, 55 ml, 0.077 mol) was slowly added. The mixture was allowed to stir for ~3 hours. The product was filtered off and washed with ET$_2$O producing Li$_2$[(Me$_2$Si(Me$_4$C$_5$)(NC$_6$H$_4$-p-n-Bu)].3/4Et$_2$O as a white solid (13.1 g, 0.033 mol).

Part 4. Li$_2$[Me$_2$Si(Me$_4$C$_5$)(NC$_6$H$_4$-p-n-Bu)].3/4Et$_2$O (3.45 g, 0.0087 mol) was suspended in ~50 ml of Et$_2$O. ZrCl$_4$ (2.0 g, 0.0086 mol) was slowly added and the mixture was allowed to stir overnight. The ether was removed via vacuum, and petroleum ether was added to precipitate out the LiCl. The mixture was filtered through Celite. The filtrate was evaporated to dryness to give a yellow solid which was recrystallized from pentane and identified as Me$_2$Si(Me$_4$C$_5$)(NC$_6$H$_4$-p-n-Bu)ZrCl$_2$.3ET$_2$O (4.2 g).

Example L

Compound L: Li$_2$[MeSi(Me$_4$C$_5$)(NC$_6$H$_4$-p-n-Bu].3/4ET$_2$O was prepared as described in Example K for the preparation of compound K, Part 3.

Part 4. Li$_2$[Me$_2$Si(Me$_4$C$_5$)(NC$_6$H$_4$-p-n-Bu].3/4Et$_2$O (3.77 g., 0.0095 mol) was suspended in ~50 ml of Et$_2$O. HfCl$_4$ (3.0 g, 0.0094 mol) was slowly added as a solid and the mixture was allowed to stir overnight. The ether was removed via vacuum and petroluem ether was added to precipitate out the LiCl. The mixture was filtered through Celite. Petroleum ether was removed via a vacuum giving an off white solid which was recrystallized from pentane. The product was identified as Me$_2$Si(Me$_4$C$_5$)(NC$_6$H$_4$-p-n-Bu)HfCl$_2$ (1.54 g, 0.0027 mol.).

Example AT

Compound AT: Part 1. MePhSiCl$_2$ (14.9 g, 0.078 mol) was diluted with 250 ml of thf. Me$_4$HC$_5$Li (10.0 go 0.078 mol) was slowly added as a solid. The reaction solution was allowed to stir overnight. The solvent was removed via a vacuum to a cold trap held at −196° C. Petroleum ether was added to precipitate out the LiCl. The mixture was filtered through Celite and the pentane was removed from the filtrate. MePhSi(Me$_4$C$_5$H)Cl (20.8 g, 0.075 mol) was isolated as a yellow viscous liquid.

Part 2. LiHN-t-Bu (4.28 g, 0.054 mol) was dissolved in ~100 ml of thf. MePhSi(C$_5$Me$_4$H)Cl (15.0 g, 0.054 mol) was added dropwise. The yellow solution was allowed to stir overnight. The solvent was removed in vacuo. Petroleum ether was added to precipitate the LiCl. The mixture was filtered through Celite, and the filtrate was evaporated. MePhSi(C$_5$Me$_4$H)(NH-t-Bu) (16.6 g, 0.053 mol) was recovered as an extremely viscous liquid.

Part 3. MePhSi(C$_5$Me$_4$H)(NH-t-Bu)(17.2 g, 0.055 mol) was diluted with ~20 ml of ether. n-BuLi (60 ml in hexane, 0.096 mol, 1.6 M) was slowly added and the reaction mixture was allowed to stir for ~3 hours. The solvent was removed in vacuo to yield 15.5 g (0.48 mol) of a pale tan solid formulated as Li$_2$[MePhSi(C$_5$Se$_4$)(N-t-Bu)].

Part 4. Li$_2$[MePhSi(C$_5$Me$_4$)(N-t-Bu)] (8.75 g, 0.027 mol) was suspended in ~125 ml of cold ether (~−30° C.). TiCl$_4$.2Et$_2$O (9.1 g, 0.027 mol) was slowly added. The reaction was allowed to stir for several hours prior to removing the ether via vacuum. A mixture of toluene and dichloromethane was then added to solubilize the product. The mixture was filtered through Celite to remove the LiCl. The solvent was largely removed via vacuum and petroleum ether was added. The mixture was cooled to maximize product precipitation. The crude product was filtered off and redissolved in toluene. The toluene insolubles were filtered off. The toluene was then reduced in volume and petroleum ether was added. The mixture was cooled to maximize precipitation prior to filtering off 3.34 g (7.76 mmol) of the yellow solid MePhSi(C$_5$Me$_4$)(N-t-Bu)TiCl$_2$.

Example BT

Compound BT: Part 1. C$_5$Me$_4$HLi (10.0 g, 0.078 mol) was slowly added to a Me$_2$SiCl$_2$ solution (11.5 ml, 0.095 mol, in 225 ml of tetrahydrofuran). The solution was stirred for 1 hour to assure a complete reaction. The solvent was then removed in vacuo. Pentane was added to precipitate the LiCl. The mixture was filtered through Celite and the solvent was removed from the filtrate in vacuo. (C$_5$Me$_4$H)SiMe$_2$Cl (15.34 g, 0.071 mol) was recovered as a pale yellow liquid.

Part 2. (C$_5$Me$_4$H)SiMe$_2$Cl (10.0 g, 0.047 mol) was diluted with ~25 ml of Et$_2$O. LiHNC$_5$H$_4$-p-n-Bu.1/10ET$_2$O (7.75 g, 0.048 mol) was added slowly. The mixture was allowed to stir for ~3 hours. The solvent was removed in vacuo. Petroleum ether was added to precipitate the LiCl, and the mixture was filtered through Celite. The solvent was removed leaving behind an orange viscous liquid, Me$_2$Si(C$_5$Me$_4$H)(HNC$_6$H$_4$-p-n-Bu) (12.7 g, 0.039 mol).

Part 3. Me$_2$Si(C$_5$Me$_4$H)(HNC$_6$H$_4$-p-n-Bu) (12.7 g, 0.039 mol) was diluted with ~50 ml of Et$_2$O. MeLi (1.4 N, 55 ml, 0.077 mol) was slowly added. The mixture was allowed to stir for ~3 hours. The product was filtered off and washed with $Et_2O$ and dried. $Li_2[Me_2Si(C_5Me_4)(NC_6H_4\text{-p-n-Bu})]$.3/4$Et_2O$ was isolated as a white solid (13.1 g, 0.033 mol).

Part 4. $Li_2[Me_2Si(C_5Me_4)(NC_6H_4\text{-p-n-Bu})]$.3/4$Et_2O$ (2.36 g, 5.97 mmol) was suspended in cold ether. $TiCl_4.2Et_2O$ (2.0 g, 5.92 mmol) was slowly added. The mixture was allowed to stir overnight. The solvent was removed via vacuum and petroleum ether and dichloromethane were added. The mixture was filtered through Celite to remove the LiCl. The solvent was removed via vacuum, and toluene and petroleum ether were added. After refrigeration, the mixture was filtered off, producing an off yellow product. This was redissolved in dichloromethane, followed by the addition of petroleum ether. The mixture was then refrigerated prior to filtering off 0.83 g (1.87 mmol) of the yellow solid, $Me_2Si(C_5Me_4)(NC_6H_4\text{-p-n-Bu})TiCl_2$.

Example CT

Compound CT: Part 1. $(C_5Me_4H)SiMe_2Cl$ was prepared as described in Example BT for the preparation of compound BT, Part 1.

Part 2. $(C_5Me_4H)SiMe_2Cl$ (8.14 g, 0.038 mol) was mixed with ~100 ml of thf. $LiHNC_6H_4\text{-p-OMe}$ (4.89 g, 0.038 mol) was slowly added and the mixture was allowed to stir for 2 hours. The solvent was removed via vacuum and petroleum ether was added to precipitate the LiCl which was filtered off. The solvent was removed from the filtrate via vacuum and the product $Me_2Si(C_5Me_4H)(NC_6H_4\text{-p-OMe})$ (9.8 g, 0.033 mol) was isolated as a viscous orange -yellow liquid.

Part 3. $Me_2Si(C_5Me_4H)(HNC_6H_4\text{-p-OMe})$ (10.0 g, 0.033 mol) was diluted with thf. MeLi (47 ml, 1.4 M in ether, 0.066 mol) was slowly added and the mixture was allowed to stir for a few hours. The solvent was then removed in vacuo leaving behind a white solid coordinated by thf. The product was formulated as $Li_2[Me_2Si(C_5Me_4)(NC_6H_4\text{-p-OMe})]$.2thf (14.7 g, 0.032 mol).

Part 4. $Li_2(Me_2Si(C_5Me_4)(NC_6H_4\text{-p-OMe})$.2thf (7.0 g, 0.015 mol) was suspended in ~125 ml of cold ether. $TiCl_4.2Et_2O$ (5.1 g, 0.015 mol) was slowly added and the mixture was allowed to stir overnight. The solvent was removed via vacuum and petroleum ether, dichloromethane and toluene were added. The mixture was filtered through Celite to remove the LiCl. The solvent was reduced in volume and petroleum ether was added. The mixture was refrigerated, after which a brown solid was filtered off. Multiple extractions and recrystallizations from toluene and petroleum ether yielded 2.3 g (5.5 mmol) of $Me_2Si(C_5Me_4)(NC_6H_4\text{-p-OMe})TiCl_2$.

Example DT

Compound DT: Part 1. $Me_2SiCl_2$ (7.5 ml, 0.062 mol) was diluted with ~30 ml of thf. A $t\text{-BuH}_4C_5Li$ solution (7.29 g, 0.057 mol, ~100 ml of thf) was slowly added, and the resulting mixture was allowed to stir overnight. The thf was removed in vacuo. Pentane was added to precipitate the LiCl, and the mixture was filtered through Celite. The pentane was removed from the filtrate leaving behind a pale yellow liquid, $(t\text{-}BuC_5H_4)SiMe_2Cl$ (10.4 g, 0.048 mol).

Part 2. $(t\text{-}BuC_5H_4)SiMe_2Cl$ (5.0 g, 0.023 mol) was added to ~50 ml of thf. $LiHN\text{-}2,5\text{-}t\text{-}Bu_2C_6H_3$ (4.94 g, 0.023 mol) was slowly added and the reaction mixture was allowed to stir for 2 hours. The solvent was removed via vacuum and petroleum ether was added to precipitate the LiCl which was filtered off. The solvent was removed from the filtrate yielding an oily/solid material, $Me_2Si(t\text{-}Bu_2C_5H_4)(HN\text{-}2,5\text{-}t\text{-}Bu_2C_6H_3)$.

Part 3. To the above material, $Me_2Si(t\text{-}BuC_5H_4)(HN\text{-}2,5\text{-}t\text{-}Bu_2C_6H_3)$ (assumed to be ~8 g, 0.021 mol), MeLi (30 ml, 1.4 N in ether, 0.042 mol) was slowly added. The mixture was allowed to stir for a few hours prior to removing the solvent via vacuum. The slightly pinkish solid was washed with ether, filtered and dried yielding 4.42 g (0.011 mol) of $Li_2[Me_2Si(t\text{-}BuC_5H_3)(N\text{-}2,5\text{-}t\text{-}Bu_2C_6H_3)]$.

Part 4. $Li_2[Me_2Si(t\text{-}BuC_5H_3)(N\text{-}2,5\text{-}t\text{-}Bu_2C_6H_3)]$ (7.6 g, 0.019 mol) was suspended in cold ether. $TiCl_4.2Et_2O$ (6.5 g, 0.019 mol) was slowly added and the mixture was allowed to stir overnight. The solvent was removed via vacuum and toluene and dichloromethane were added. The mixture was filtered through Celite to remove the LiCl. The filtrate was reduced in volume and petroleum ether was added. The mixture was chilled to maximize precipitation. A dark yellow solid was filtered off and was recrystallized from toluene and petroleum ether giving a tan solid. A total of 1.6 g (3.2 mmol) of $Me_2Si(t\text{-}BuC_5H_3)(N\text{-}2,5\text{-}t\text{-}Bu_2C_6H_3)TiCl_2$ was isolated.

Example ET

Compound ET: Part 1. $LiC_9H_7$ (40 g, 0.33 mol, lithiated indene=Li (Hind)) was slowly added to $Me_2SiCl_2$ (60 ml, 0.49 mol) in ether and thf. The reaction was allowed to stir for 1.5 hours prior to removing the solvent via vacuum. Petroleum ether was then added, and the LiCl was filtered off. The solvent was removed from the filtrate via vacuum, leaving behind the pale yellow liquid, $(Hind)Me_2SiCl$ (55.7 g, 0.27 mol).

Part 2. $(Hind)Me_2SiCl$ (20.0 g, 0.096 mol) was diluted with ether. $LiHN\text{-}t\text{-}Bu$ (7.6 g, 0.096 mol) was slowly added and the mixture was allowed to stir overnight. The solvent was removed via vacuum and. petroleum ether and toluene were added. The LiCl was filtered off and the solvent was removed via vacuum to give the product, $Me_2Si(Hind)(HN\text{-}t\text{-}Bu)$.

Part 3. $Me_2Si(Hind)(HN\text{-}t\text{-}Bu)$ (21 g, 0.086 mol) was diluted with a mixture of petroleum ether and diethyl ether. t-BuLi (108 ml, 1.6 M in hexanes, 0.17 mol) was slowly added and the mixture was allowed to stir overnight. The solvent was removed via vacuum and the remaining solid was washed with petroleum ether and filtered off. $Li_2[Me_2Si(ind)(N\text{-}t\text{-}Bu)].1/4Et_2O$ was isolated as a pale yellow solid (26 g, 0.094 mol).

Part 4. $Li_2[Me_2Si(ind)(N\text{-}t\text{-}Bu)].1/4Et_2O$ (10 g, 0.036 mol) was dissolved in ether. $TiCl_4.2Et_2O$ (12.1 g, 0.036 mol) was aded to the cold solution. The reaction was allowed to stir overnight prior to removal of the solvent via vacuum. A mixture of toluene and dichloromethane were added and the mixture was filtered through Celite to remove the LiCl. The solvent was removed and hot toluene was added. The insolubles were filtered off. The solution was reduced in volume and petroleum ether was added. The mixture was chilled prior to filtering off the solid, $Me_2Si(ind)(N\text{-}t\text{-}Bu)TiCl_2$, which was recrystallized several times. The final yield was 2.5 g (6.8 mmol).

Example FT

Compound FT: Part 1. $(C_5Me_4H)SiMe_2Cl$ was prepared as described in Example BT for the preparation of compound BT, Part 1.

Part 2. $(C_5Me_4H)SiMe_2Cl$ (5.19 g, 0.024 mol) was slowly added to a solution of $LiHNC6H_{11}$ (2.52 g, 0.024 mol) in ~125 Ml of thf. The solution was allowed to stir for several hours. The thf was removed via vacuum and petroleum ether was added to precipitate the LiCl which was filtered off. The solvent was removed from the filtrate via vacuum yielding 6.3 g (0.023 mol) of the yellow liquid, $Me_2Si(C_5Me_4H)(HNC_6H_{11})$.

Part 3. $Me_2Si(C_5Me_4H)(HNC_6H_{11})$ (6.3 g, 0.023 mol) was diluted with ~100 ml of ether. MeLi (33 ml, 1.4 M in ether, 0.046 mol) was slowly added and the mixture was allowed to stir for 0.5 hours prior to filtering off the white solid. The solid was washed with ether and vacuum dried. $Li_2[Me_2Si(C_5Me_4)(NC_6H_{11})]$ was isolated in a 5.4 g (0.019 mol) yield.

Part 4. $Li_2[(Me_2Si(C_5Me_4)(NC_6H_{11})]$ (2.57 g, 8.90 mmol) was suspended in ~50 ml of cold ether. $TiCl_4 \cdot 2Et_2O$ (3.0 g, 8.9 mmol) was slowly added and the mixture was allowed to stir overnight. The solvent was removed via vacuum and a mixture of toluene and dichloromethane was added. The mixture was filtered through Celite to remove the LiCl byproduct. The solvent was removed from the filtrate and a small portion of toluene was added followed by petroleum ether. The mixture was chilled in order to maximize precipitation. A brown solid was filtered off which was initially dissolved in hot toluene, filtered through Celite, and reduced in volume. Petroleum ether was then added. After refrigeration, an olive green solid was filtered off. This solid was recrystallized twice from dichloromethane and petroleum ether to give a final yield of 0.94 g (2.4 mmol) of the pale olive green solid, $Me_2Si(C_5Me_4)(NC_6H_{11})TiCl$.

Example GT

Compound GT: Part 1. $Me_2SiCl_2$ (150 ml, 1.24 mol) was diluted with ~200 ml of $Et_2O$. $Li(C_{13}H_9) \cdot Et_2O$ (lithiated fluorene etherate, 28.2 g, 0.11 mol) was slowly added. The reaction was allowed to stir for ~1 hour prior to removing the solvent via vacuum. Toluene was added and the mixture was filtered through Celite to remove the LiCl. The solvent was removed from the filtrate, leaving behind the off-white solid, $Me_2Si(C_{13}H_9)Cl$ (25.4 g, 0.096 mol).

Part 2. $Me_2Si(C_{13}H_9)Cl$ (8.0 g, 0.031 mol) was suspended in ether and thf in a ratio of 5:1. $LiHNC_6H_{11}$ (3.25 g, 0.031 mol) was slowly added. The reaction mixture was allowed to stir overnight. After removal of the solvent via vacuum, toluene was added and the mixture was filtered through Celite to remove the LiCl. The. filtrate was reduced in volume to give a viscous orange liquid. To this liquid which was diluted in $Et_2O$, 43 ml of 1.4 M MeLi (0.060 mol) was added slowly. The mixture was allowed to stir overnight. The solvent was removed in vacuo to produce 13.0 g (0.031 mol) of $Li_2[Me_2Si(C_{13}H_8)(NC_6H_{11})] \cdot 1.25Et_2O$.

Part 3. $Li_2[Me_2Si(C_{13}H_8)(NC_6H_{11})] \cdot 1.25Et_2O$ (6.5 g, 0.015 mol) was dissolved in cold ether. $TiCl_4 \cdot 2Et_2O$ (5.16 g, 0.015 mol) was slowly added. The mixture was allowed to stir overnight. The solvent was removed via vacuum and methylene chloride was added. The mixture was filtered through Celite to remove the LiCl. The filtrate was reduced in volume and petroleum ether was added. This was refrigerated to maximize precipitation prior to filtering off the solid. Since the solid collected was not completely soluble in toluene, it was mixed with toluene and filtered. The filtrate was reduced in volume and petroleum ether was added to induce precipitation. The mixture was refrigerated prior to filtration. The red-brown solid $Me_2Si(C_{13}H_8)(NC_6H_{11})TiCl_2$ was isolated (2.3 g, 5.2 mol).

Example HT

Compound HT: Part 1. $(C_5Me_4H)SiMe_2Cl$ was prepared as described in Example BT for the preparation of compound BT, Part 1.

Part. 2 LiHNPh (4.6 g, 0.046 mol) was dissolved in ~100 ml of thf. $(C_5Me_4H)SiMe_2Cl$ (10.0 g, 0.047 mol) was slowly added. The mixture was allowed to stir overnight. The thf was removed in vacuo. Petroleum ether and toluene were added to precipitate the LiCl, and the mixture was filtered through Celite. The solvent was removed, leaving behind a dark yellow liquid, $Me_2Si(C_5Me_4H)(NHPh)$ (10.5 g, 0.039 mol).

Part 3. $Me_2Si(C_5Me_4H)(NHPh)$ (9.33 g, 0.034 mol) was diluted with ~30 ml of ether. MeLi (1.4 M in ether, 44 ml, 0.062 mol) was slowly added and the reaction was allowed to stir for 2 hours. After reducing the volume of the solvent, the resulting white solid, $Li_2[Me_2Si(C_5Me_4)(NPh)] \cdot 1/2Et_2O$ (9.7 g, 0.030 mol), was filtered off washed with ether and dried.

Part 4. $Li_2[Me_2Si(C_5Me_4(NPh)] \cdot 1/2Et_2O$ (4.3 g, 0.013 mol) was suspended in ~50 ml of cold ether. $TiCl_4 \cdot 2Et_2O$ (4.10 g, 0.012 mol) was slowly added, and the mixture was allowed to stir for several hours. The solvent was removed in vacuo, and toluene and dichloromethane were added to solubilize the product. The mixture was filtered through Celite to remove the LiCl. The solvent was removed in vacuo and a small portion of toluene was added along with petroleum ether. The mixture was refrigerated in order to maximize precipitation of a tan solid which was filtered off. The solid was washed with a small portion of toluene and the remaining solid was redissolved in hot toluene and filtered through Celite to remove the toluene insolubles. The toluene was then removed to produce 2.32 g (5.98 mmol) of the yellow solid, $Me_2Si(C_5Me_4)(NPh)TiCl_2$.

Example IT

Compound IT: Part 1. $(C_5Me_4H)SiMe_2Cl$ was prepared as described in Example BT for the preparation of Compound BT, part 1.

Part 2. $(C_5Me_4H)SiMe_2Cl$ (10.0 g, 0.047 mol) was slowly added to a suspension of LiHN-t-Bu (3.68 g, 0.047 mol, ~100ml thf). The mixture was stirred overnight. The thf was then removed via a vacuum to a cold trap held at −196° C. Petroleum ether was aded to precipitate out the LiCl. The mixture was filtered through Celite. The solvent was removed from the filtrate. $Me_2Si(C_5Me_4H)(NH-t-Bu)$ (11.14 g, 0.044 mol) was isolated as a pale yellow liquid.

Part 3. $Me_2Si(C_5Me_4H)(NH-t-Bu)$ (11.14 g, 0.044 mol) was diluted with ~100 ml of ether. MeLi (1.4 M, 64 ml, 0.090 mol) was slowly added. The mixture was allowed to stir for ½ hour after the final addition of MeLi. The ether was reduced in volume prior to filtering off the product. The product, $[Me_2Si(C_5Me_4)(N-t-Bu)]Li_2$, was washed with several small portions of ether, then vacuum dried.

Part 4. $[Me_2Si(C_5Me_4)(N-t-Bu)Li_2$ (6.6 g, 0.025 mol) was suspended in cold ether. $TiCl_4 \cdot 2Et_2O$ (8.4 g, 0.025 mol) was slowly added and the resulting mixture was allowed to stir overnight. The ether was removed via a vacuum to a cold trap held at −196° C. Methylene chloride was added to precipitate out the LiCl. The mixture was filtered through Celite. The solvent was significantly reduced in volume and petroleum ether was added to precipitate out the product. This mixture was refrigerated prior to filtration in order to maximize precipitation. $Me_2Si(C_5Me_4)(N-t-Bu)TiCl_2$ was isolated (2.1 g, 5.7 mmol).

Example JT

Compound JT: Part 1. $(C_5Me_4H)SiMe_2Cl$ was prepared as described in Example BT for the preparation of Compound BT, Part 1.

Part 2. $(C_5Me_4H)SiMe_2Cl$ (8.0 g, 0.037 mol) was slowly added to a suspension of $LiHNC_{12}H_{23}$ ($C_{12}H_{23}$=cyclododecyl, 7.0 g, 0.037 mol, ~80 ml thf). The mixture was stirred overnight. The thf was then removed via a vacuum to a cold trap held at −196° C. Petroleum ether and toluene was added to precipitate out the LiCl. The mixture was filtered through Celite. The solvent was removed from the filtrate. $Me_2Si(C_5Me_4H)(NHC_{12}H_{23})$ (11.8 g, 0.033 mol) was isolated as a pale yellow liquid.

Part 3. $Me_2Si(C_5Me_4H)(NHC_{12}H_{23})$ (11.9 g, 0.033 mol) was diluted with ~150 ml of ether. MeLi (1.4 M, 47 ml, 0.066 mol) was slowly added. The mixture was allowed to stir for 2 hours after the final addition of MeLi. The ether was reduced in volume prior to filtering off the product. The product, $[Me_2Si(C_5Me_4)(NC_{12}H_{23})]Li_2$, was washed with several small portions of ether, then vacuum dried to yield 11.1 g (0.030 mol) of product.

Part 4. $[Me_2Si(C_5Me_4)(NC_{12}H_{23})]Li_2$ (3.0 g, 0.008 mol) was suspended in cold ether. $TiCl_4.2Et_2O$ (2.7 g, 0.008 mol) was slowly added and the resulting mixture was allowed to stir overnight. The ether was removed via a vacuum to a cold trap held at −196° C. Methylene chloride was added to precipitate out the LiCl. The mixture was filtered through Celite. The solvent was significantly reduced in volume and petroleum ether was added to precipitate out the product. This mixture was refrigerated prior to filtration in order to maxmize precipitation. The solid collected was recrystallized from methylene chloride and $Me_2Si(C_5Me_4)$ $(NC_{12}H_{23})TiCl_2$ was isolated (1.0 g, 2.1 mmol).

Examples 1–70 of Polymerization

Example 1

Polymerization—Compound A

The polymerization run was performed in a 1-liter autoclave reactor equipped with a paddle stirrer, an external water jacket for temperature contorl, a regulated supply of dry nitrogen, ethylene, propylene, 1-butene and hexane, and a septum inlet for introduction of other solvents, transition metal compound and alumoxane solutions. The reactor was dried and degassed thoroughly prior to use. A typical run consisted of injecting 400 ml of toluene, 6 ml of 1.5 M MAO, and 0.23 mg of compound A (0.2 ml of a 11.5 mg in 10 ml of toluene solution) into the reactor. The reactor was then heated to 80° C. and the ethylene (60 psi) was introduced into the system. The solvent was evaporated off of the polymer by a stream of nitrogen. Polyethylene was recovered (9.2 g, Mw=257,200, MWD=2.275).

Example 2

Polymerization Compound A

The polymerization was carried out as in Example 1 with the following changes: 300 ml of toluene, 3 ml of 1.5 M MAO, and 0.115 mg of compound A (0.1 ml of a 11.5 mg in 10 ml of toluene solution). Polyethylene was recovered (3.8 g, MW=359,800, MWD=2.425).

Example 3

Polymerization—Compound A

The polymerization was carried out as in Example 2 using the identical concentrations. The difference involved running the reaction at 40° C. rather than 80° C. as in the previous example. Polyethylene was recovered (2.4 g, MW=635,000, MWD=3.445).

Example 4

Polymerization—Compound A

The polymerization was carried out as in Example 1 except for the use of 300 ml of hexane in place of 400 ml of toluene. Polyethylene was recovered (5.4 g, MW=212,600, MWD=2.849).

Example 5

Polymerization—Compound A

Using the same reactor design and general procedure as in Example 1, 300 ml of toluene, 200 ml of propylene, 6.0 ml of 1.5 M MAO, and 0.46 mg of compound A (0.4 ml of a 11.5 mg in 10 ml of toluene solution) was introduced into the reactor. The reactor was heated to 80° C., the ethylene was added (60 psi), and the reaction was allowed to run for 30 minutes, followed by rapidly cooling and venting the system. After evaporation of the solvent, 13.3 g of an ethylene-propylene copolymer was recovered (MW=24,900, MWD=2.027, 73.5 SCB/1000C by IR).

Example 6

Polymerization—Compound A

The polymerization was carried out as in Example 5 except with the following changes: 200 ml of toluene and 0.92 mg of compound A (0.8 ml of a 11.5 mg in 10 ml of toluene solution). The reaction temperature was also reduce to 50° C. An ethylene-propylene copolymer was recovered (6.0 g, MW=83,100, MWD=2.370, 75.7 SCB/1000C by IR).

Example 7

Polymerization—Compound A

Using the same reactor design and general procedure as in Example 1, 150 ml of toluene, 100 ml of 1-butene, 6.0 ml of 1.5 M MAO, and 2.3 mg of compound A (2.0 ml of a 11. 5 mg in 10 ml of toluene solution) were added to the reactor. The reactor was heated at 50° C., the ethylene was introduced (65 psi), and the reaction was allowed to run for 30 minutes, followed by rapidly cooling and venting the system. After evaporation of the toluene, 25.4 g of an ethylene-1-butene copolymer was recovered (MW=184,500, MWD=3.424, 23.5 SCB/1000C by $^{13}C$ NMR and 21.5 SCB/1000C by IR).

Example 8

Polymerization—Compound A

The polymerization was carred out as in Example 7 except with the following changes: 100 ml of toluene and 150 ml of 1-butene. An ethylene-1-butene copolyer was recovered (30.2 g, MW=143,500, MWD=3.097, 30.8 SCB/1000C by $^{13}C$ NMR and 26.5 SCB/1000C by IR).

Example 9

Polymerization—Compound A

The polymerization was carried out as in Example 7 except with the following changes: 200 ml of toluene, 8.0 ml of 1.0 M MAO, and 50 ml of 1-butene. An ethylene-1-butene copolymer was recovered (24.9 g, MW=163,200, MWD=3.290, 23.3 SCB/1000C by $^{13}$C NMR and 18.9 SCB/1000C by IR).

Example 10

Polymerization—Compound A

The polymerization was carried out as in Example 9 except for the replacement of 200 ml of toluene with 200 ml of hexane. An ethylene-1-butene copolymer was recovered (19.5 g, MW=150,600, MWD=3.510, 12.1 SCB/1000C by $^{13}$C NMR and 12.7 SCB/1000C by IR).

Example 11

Polymerization—Compound A

The polymerization was carried out as in Example 10 except with the following changes: 150 ml of hexane, and 100 ml of 1-butene. An ethylene-1-butene copolymer was recovered (16.0 g, MW=116,200, MWD=3.158, 19.2 SCB/1000C by $^{13}$C NMR and 19.4 SCB/1000C by IR).

Example 12

Polymerization—Compound A

Using the same reactor design and general procedure as described in Example 1, 400 ml of toluene, 5.0 ml of 1.0 M MAO, and 0.2 ml of a preactivated compound A solution (11.5 mg of compound A dissolved in 9.0 ml of toluene and 1.0 ml of 1.0 M MAO) were added to the reactor. The reactor was heated to 80° C., and ethylene was introduced (60 psi), and the reactor was allowed to run for 30 minutes, followed by rapidly cooling and venting the system. After evaporation of the solvent, 3.4 g of polyethylene was recovered (MW=285,000, MWD=2.808).

Example 13

Polymerization—Compound A

A polymerization was carried out as in Example 12 with exception of aging the preactivated compound A solution by one day. Polyethylene was recovered (2.0 g, MW=260,700, MWD=2.738).

Example 14

Polymerization—Compound A

Using the same reactor design and general procedure as described in Example 1, 400 ml of toluene, 0.25 ml of 1.0 M MAO, and 0.2 ml of a preactivated compound A solution (11.5 mg of compound A dissolved in 9.5 ml of toluene and 0.5 ml of 1.0 M MAO) were added into the reactor. The reactor was heated to 80° C. and ethylene was introduced (60 psi), and the reactor was allowed to run for 30 minutes, followed by rapidly cooling and venting the system. After evaporation of the solvent, 1.1 g of polyethylene was recovered (MW=479,600, MWD=3.130).

Example 15

Polymerization—Compound A

Using the same reactor design and general procedure as described in Example 1, 400 ml of toluene and 2.0 ml of a preactivated compound A solution (11.5 mg of compound A dissolved in 9.5 ml of toluene and 0.5 ml of 1.0 M MAO) were added into the reactor. The reactor was heated to 80° C. and ethylene was introduced (60 psi), and the reaction was allowed to run for 30 minutes, followed by rapidly cooling and venting the system. After evaporation of the solvent, 1.6 g of polyethylene was recovered (MW=458,800, MWD=2.037).

Example 16

Polymerization—Compound A

Using the general procedure as described in Example 1, 400 ml of toluene, 5.0 ml of 1.0 M MAO, 0.23 mg of compound A (0.2 ml of a 11.5 mg in 10 ml of toluene solution) was added to the reactor. The reactor was heated to 80° C., the ethylene introduced (400 psi), and the reaction was allowed to run for 30 minutes, followed by rapidly cooling and venting the system. After evaporation of the solvent, 19.4 g of polyethylene was recovered (MW=343,700, MWD=3.674).

Example 17

Polymerization—Compound A

The polymerization was performed in a stirred 100 ml stainless steel autoclave which was equipped to perform polymerizations at pressures up to 40,000 psi and temperatures up to 300° C. The reactor was purged with nitrogen and heated to 160° C. Compound A and alumoxane solutions were prepared in separate vials. A stock solution was prepared by dissolving 26 mg of compound A in 100 ml of toluene. The compound A solution was prepared by diluting 0.5 ml of the stock solution with 5.0 ml of toluene. The alumoxane solution consisted of 2.0 ml of a 4% MAO solution added to 5.0 ml of toluene. The compound A solution was added to the alumoxane solution, then 0.43 ml of the mixed solutions were transferred by nitrogen pressure into a constant-volume injection tube. The autoclave was pressurized with ethylene to 1784 bar and was stirred at 1500 rpm. The mixed solutions were injected into the stirred reactor with excess pressure, at which time a temperature rise of 4° C. was observed. The temperature and pressure were recorded continuously for 120 seconds, at which time the contents of the autoclave were rapidly vented into a receiving vessel. The reactor was washed with xylene to recover any additional polymer remaining. These washings were combined with the polymer released when the autoclave was vented to yield 0.7 g of polyethylene (MW=245,500, MWD=2.257).

Example 18

Polymerization—Compound B

Using the general procedure described in Example 1, 400 ml of toluene, 5.0 ml of 1.0 M MAO and 0.278 mg of compound B (0.2 ml of a 13.9 mg in 10 ml of toluene solution) were added to the reactor. The reactor was heated to 80° C. and the ethylene (60 psi) was introduced into the system. The polymerization reaction was limited to 10 minutes. The reaction was ceased by rapidly cooling and venting the system. The solvent was evaporated off the polymer by a stream of nitrogen. Polyethylene was recovered (9.6 g, MW=241,200, MWD=2.628).

Example 19

Polymerization—Compound C

Using the general procedures described in Example 1, 300 ml of toluene, 4.0 ml of 1.0 M MAO and 0.46 mg of compound C (0.4 ml of a 11.5 mg in 10 ml of toluene solution) was added to the reactor. The reactor was heated to 80° C. and the ethylene (60 psi) was introduced into the system. The polymerization reaction was limited to 30 minutes. The reaction was ceased by rapidly cooling and venting the system. The solvent was evaporated off the polymer by a stream of nitrogen. Polyethylene was recovered (1.7 g, MW=278,400, MWD=2.142).

Example 20

Polymerization—Compound D

Using the general procedure described in Example 1, 400 ml of toluene, 5.0 ml of 1.0 M MAO and 0.278 mg of compound D (0.2 ml of a 13.9 mg in 10 ml of toluene solution) was added to the reactor. The reactor was heated to 80° C. and ethylene (60 psi) was introduced into the system. The polymerization reaction was limited to 30 minutes. The reaction was ceased by rapidly cooling and venting the system. The solvent was evaporated off the polymer by a stream of nitrogen. Polyethylene was recovered (1.9 g, MW=229,700, MWD=2.618).

Example 21

Polymerization—Compound E

Using the general procedure described in Example 1, 300 ml of hexane, 9.0 ml of 1.0 M MAO and 0.24 mg of compound E (0.2 ml of a 12.0 mg in 10 ml of toluene solution) was added to the reactor. The reactor was heated to 80° C. and ethylene (60 psi) was introduced into the system. The polymerization reaction was limited to 30 minutes. The reaction was ceased by rapidly cooling and venting the system. The solvent was evaporated off the polymer by a stream of nitrogen. Polyethylene was recovered (2.2 g, MW=258,200, MWD=2.348).

Example 22

Polymerization—Compound E

The polymerization was carried out as in Example 1 except with the following reactor conditions: 200 ml of toluene, 100 ml of 1-butene, 9.0 ml of 1.0 M MAO and 2.4 mg of compound E (2.0 ml of a 12.0 mg in 10 ml of toluene solution) at 50° C. The reactor was pressurized with ethylene (65 psi), and the reaction was allowed to run for 30 minutes, followed by rapidly cooling and venting the system. After evaporation of the solvent, 1.8 q of an ethylene-1-butene copolymer was recovered (MW=323,600, MWD=2.463, 33.5 SCB/1000C by IR).

Example 23

Polymerization—Compound F

The polymerization was carried out as in Example 1 with the following reactor conditions: 400 ml of toluene, 5.0 ml of 1.0 M MAO, 0.242 mg of compound F (0.2 ml of a 12.1 mg in 10 ml of toluene solution), 80° C., 60 psi ethylene, 30 minutes. The run provided 5.3 g of polyethylene (MW=319,900, MWD=2.477).

Example 24

Polymerization—Compound F

The polymerization was carried out as in Example 1 with the following reactor conditions: 150 ml of toluene, 100 ml of 1-butene, 9.0 ml of 1.0 M MAO, 2.42 mg of compound F (2.0 ml of a 12.1 mg in 10 ml of toluene solution), 50° C., 65 psi ethylene, 30 minutes. The run provided 3.5 g of an ethylene-1-butene copolymer (MW=251,300, MWD=3.341, 33.3 SCB/1000C by IR).

Example 25

Polymerization—Compound G

The polymerization was carried out as in Example 1 with the following reactor conditions: 400 ml of toluene, 5.0 ml of 1.0 M MAO, 0.29 mg of compound G (0.2 ml of a 14.5 mg in 10 ml of toluene solution), 80° C., 60 psi ethylene, 30 minutes. The run provided 3.5 g of polyethylene (MW=237,300, MWD=2.549).

Example 26

Polymerization—Compound G

The polymerization was carried out as in Example 1 with the following reactor conditions: 150 ml of toluene, 100 ml of 1-butene, 7.0 ml of 1.0 M MAO, 2.9 mg of compound G (2.0 ml of a 14. 5 mg in 10 ml of toluene solution), 50° C., 65 psi ethylene, 30 minutes. The run provided 7.0 g of an ethylene-1-butene copolymer (MW=425,000, MWD=2.816, 27.1 SCB/1000C by IR).

Example 27

Polymerization—Compound H

The polymerization was carried out as in Example 1 with the following reactor conditions: 400 ml of toluene, 5.0 ml of 1.0 M MAO, 0.266 mg of compound H (0.2 ml of a 13.3 mg in 10 ml of toluene solution), 80° C., 60 psi ethylene, 30 minutes. The run provided 11.1 g of polyethylene (MW=299,800, MWD=2.569).

Example 28

Polymerization—Compound H

The polymerization was carried out as in Example 1 with the following reactor conditions: 150 ml of toluene, 100 ml of 1-butene, 7.0 ml of 1.0 M MAO, 2.66 mg of compound H (2.0 ml of a 13.3 mg in 10 ml of toluene solution), 50° C., 65 psi ethylene, 30 minutes. The run provided 15.4 g of an ethylene-1-butene copolymer (MW=286,600, MWD=2.980, 45.4 SCB/1000C by Example 29

Polymerization—Compound I

The polymerization was carried out as in Example 1 with the following reactor conditions: 400 ml of toluene, 5.0 ml of 1.0 MAO, and 0.34 mg of compound I (0.2 ml of a 17.0 mg in 10 ml of toluene solution). The reactor was heated to 80° C., the ethylene was introduced (60 psi), and the reaction was allowed to run for 30 minutes, followed by rapidly cooling and venting the system. After evaporation of the solvent, 0.9 g of polyethylene was recovered (MW=377,000, MWD=1.996).

Example 30

Polymerization—Compound J

The polymerization was carried out as in Example 1 with the following reactor conditions: 400 ml of toluene, 5.0 ml of 1.0 M MAO, 0.318 mg of compound J (0.2 ml of a 15.9 mg in 10 ml of toluene solution), 80° C., 60 psi ethylene, 30 minutes. The run provided 8.6 g of polyethylene (MW=321,000, MWD=2.803).

Example 31

Polymerization—Compound J

The polymerization was carried out as in Example 1 with the following reactor conditions: 150 ml of toluene, 100 ml of 1-butene, 7.0 ml of 1.0 M MAO, 3.18 mg of compound J (2.0 ml of a 15.9 mg in 10 ml of toluene solution), 50° C., 65 psi ethylene, 30 minutes. The run provided 11.2 g of an ethylene-1-butene copolymer (MW=224,800, MWD=2.512, 49.6 SCB/1000C by IR technique, 55.4 SCB/1000C by NMR).

Example 32

Polymerization—Compound K

The polymerization was carried out as in Example 1 with the following reactor conditions: 300 ml of toluene, 5.0 ml of 1.0 M MAO, 0.272 mg of compound K (0.2 ml of a 13.6 mg in 10 ml of toluene solution), 80° C., 60 psi ethylene, 30 minutes. The run provided 26.6 g of polyethylene (MW=187,300, MWD=2.401).

Example 33

Polymerization—Compound K

The polymerization was carried out as in Example 1 with the following reactor conditions: 150 ml of toluene, 100 ml of 1-butene, 7.0 ml of a 1.0 M MAO, 2.72 mg of compound K (2.0 ml of a 13.6 mg in 10 ml of toluene solution), 50° C., 65 psi ethylene, 30 minutes. The run provided 3.9 g of an ethylene-1-butene copolymer (MW=207,600, MWD=2.394, 33.9 SCB/1000C by IR).

Example 34

Polymerization—Compound L

The polymerization was carried out as in Example 1 with the following reactor conditions: 400 ml of toluene, 5.0 ml of 1.0 M MAO, 0.322 mg of compound L (0.2 ml of a 16.1 mg in 10 ml of toluene solution), 80° C., 60 psi ethylene, 30 minutes. The run provided 15.5 g of polyethylene (MW=174,300, MWD=2.193).

Example 35

Polymerization—Compound A

The polymerization was carried out as in Example 1 with the following reactor contents: 250 ml of toluene, 150 ml of 1-hexene, 7.0 ml of 1.0 M MAO and 2.3 mg of compound A (2.0 ml of a 11.5 mg in 10 ml of toluene solution) at 50° C. The reactor was pressurized with ethylene (65 psi), and the reaction was allowed to run for 30 minutes, followed by rapidly cooling and venting the system. After evaporation of the solvent, 26.5 g of an ethylene-1-hexane copolymer was recovered (MW=222,800, MWD=3.373, 39.1 SCB/1000C by IR).

Example 36

Polymerization—Compound A

The polymerization was carried out as in Example 1 with the following reactor contents: 300 ml of toluene, 100 ml of 1-octene, 7.0 ml of 1.0 M MAO and 2.3 mg of compound A (2.0 ml of a 11.5 mg in 10 ml of toluene solution) at 50° C. The reactor was pressurized with ethylene (65 psi), and the reaction was allowed to run for 30 minutes, followed by rapidly cooling and venting the system. After evaporation of the solvent, 19.7 g of an ethylene-1-octene copolymer was recovered (MW=548,600, MWD=3.007, 16.5 SCB/1000C by $^{13}$C NMR).

Example 37

Polymerization—Compound A

The polymerization was carried out as in Example 1 with the following reactor conditions: 300 ml of toluene, 100 ml of 4-methyl-1-pentene, 7.0 ml of 1.0 M MAO and 2.3 mg of compound A (2.0 ml of a 11.5 mg in 10 ml of toluene solution) at 50° C. The reactor was pressurized with ethyleme (65 psi), and the reaction was allowed to run for 30 minutes, followed by rapidly cooling and venting the system. After evaporation of the solvent, 15.1 g of an ethylene-4-methyl-1-pentene copolymer was recovered (MW=611,800, MWD=1.683, 1.8 mole % determined by $^{13}$C NMR).

Example 38

Polymerization—Compound A

The polymerization was carried out as in Example 1 with the following reactor conditions: 300 ml of toluene, 100 ml of a 2.2 M norbornene in toluene solution, 7.0 ml of 1.0 M MAO and 2.3 mg of compound A (2.0 ml of a 11.5 mg in 10 ml of toluene solution) at 50° C. The reactor was pressurized with ethylene (65 psi), and the reaction was allowed to run for 30 minutes, followed by rapidly cooling and venting the system. After evaporation of the solvent, 12.3 g of an ethylene-norbornene copolymer was recovered (MW=812,600, MWD=1.711, 0.3 mole % determined by $^{13}$C NMR).

Example 39

Polymerization—Compound A

The polymerization was carried out as in Example 1 with the following reactor contents: 300 ml of toluene, 100 ml of cis-1,4-hexadiene, 7.0 ml of 1.0 M MAO and 2.3 mg of compound A (2.0 ml of a 11.5 mg in 10 ml of toluene solution) at 50° C. The reactor was pressurized with ethylene (65 psi), and the reaction was allowed to run for 30 minutes, followed by rapidly cooling and venting the system. After evaporation of the solvent, 13.6 g of an ethylene-cis-1,4-hexadiene copolymer was recovered (MW=163,400, MWD=2.388, 2.2 mole % determined $^{13}$C NMR).

Example 40

Polymerization—Compound AT

The polymerization run was performed in a 12-liter autoclave reactor equippped with a paddle stirrer, an external water jacket for temperature control, a regulated supply of dry nitrogen, ethylene, propylene, 1-butene and hexane, and a septum inlet for introduction of other solvents or comonomers, transition metal compound and alumoxane solutions. The reactor was dried and degassed thoroughly prior to use. A typical run consisted of injecting 400 ml of toluene, 5 ml of 1.0 M MAO, 0.206 mg compound AT (0.2 ml of a 10.3 mg in 10 ml of toluene solution) into the reactor. The reactor was then heated to 80° C. and the ethylene (60 psi) was introduced into the system. The polymerization reaction was limited to 30 minutes. The reaction was ceased by rapidly cooling and venting the system. The solvent was evaporated off of the polymer by a stream of nitrogen. Polyethylene was recovered (11.8 g, MW=279,700, MWD= 2.676).

Example 41

Polymerization—Compound AT

Using the same reactor design and general procedure as described in Example 40, 400 ml of toluene, 5.0 ml of 1.0 M MAO, and 0.2 ml of a preactivated compound AT solution (10.3 mg of compound AT dissolved in 9.5 ml of toluene and 0.5 ml of 1.0 M MAO) were added to the reactor. The reactor was heated to 80° C., the ethylene was introduced (60 psi), and the reaction was allowed to run for 30 minutes, followed by rapidly cooling and venting the system. After evaporation of the solvent, 14.5 g of polyethylene was recovered (MW= 406,100, MWD=2.486).

Example 42

Polymerization—Compound AT

Using the same reactor design and general procedure described in Example 40, 300 ml of toluene, 100 ml of 1-hexene, 7.0 ml of 1.0 M MAO, and 1.03 mg of compound AT (1.0 ml of 10.3 mg in 10 ml of toluene solution) were added to the reactor. The reactor was heated at 80° C., the ethylene was introduced (65 psi), and the reaction was allowed to run for 10 minutes, followed by rapidly cooling and venting the system. After evaporation of the toluene, 48.6 g of an ethylene-1-hexene copolymer was recovered (MW=98,500, MWD=1.745, 117 SCB/1000C by $^{13}C$ NMR).

Example 43

Polymerization—Compound AT

Using the same reactor design and general procedure described in Example 40, 375 ml of toluene, 25 ml of 1-hexene, 7.0 ml of 1.0 M MAO, and 1.03 mg of compound AT (1.0 ml of a 10.3 mg in 10 ml of toluene solution) were added to the reactor. The reactor was heated at 80° C., the ethylene was introduced (65 psi), and the reaction was allowed to run for 10 minutes, followed by rapidly cooling and venting the system. After evaporation of the toluene, 29.2 g of an ethylene-1-hexene copolymer was recovered (MW=129,800, MWD=2.557, 53.0 SCB/1000C by $^{13}C$ NMR).

Example 44

Polymerization—Compound AT

Using the same reactor design and general procedure described in Example 40, 375 ml of toluene, 25 ml of 1-hexene, 7.0 ml of 1.0 M MAO, and 1.03 mg of compound AT (1.0 ml of 10.3 mg in 10 ml of toluene solution) were added to the reactor. The reactor was heated at 50° C., the ethylene was introduced (65 psi), and the reaction was allowed to run for 10 minutes, followed by rapidly cooling and venting the system. After evaporation of the toluene, 15.0 g of an ethylene-1-hexene copolymer was recovered (MW=310,000, MWD=2.579, 47.2 SCB/1000C by $^{13}C$ NMR).

Example 45

Polymerization—Compound AT

Using the same reactor design and general procedure described in Example 40, 300 ml of toluene, 100 ml of propylene, 7.0 ml of 1.0 M MAO, and 2.06 mg of compound AT (2.0 ml of a 10.3 mg in 10 ml of toluene solution) were added to the reactor. The reactor was heated at 80° C., the ethylene was introduced (65 psi), and the reaction was allowed to run for 10 minutes, followed by rapidly cooling and venting the system. After evaporation of the toluene, 46.0 g of an ethylene-propylene copolymer was recovered (MW=110,200, MWD=5.489, 20 wt % ethylene by IR).

Example 46

Polymerization—Compound AT

Using the same reactor design and general procedure described in Example 40, 300 ml of toluene, 100 ml of 1-butene, 7.0 ml of 1.0 M MAO, and 1.03 mg of compound AT (1.0 ml of a 10.3 mg in 10 ml of toluene solution) were added to the reactor. The reactor was heated at 80° C., the ethylene was introduced (65 psi), and the reaction was allowed to run for 10 minutes, followed by rapidly cooling and venting the system. After evaporation of the toluene, 35.1 g of an ethylene-1-butene copolymer was recovered (MW=94,400, MWD=2.405, 165 SCB/1000C by $^{13}C$ NMR).

Example 47

Polymerization—Compound AT

Using the same reactor design and general procedure described in Example 40, 300 ml of toluene, 100 ml of 1-octene, 7.0 ml of 1.0 M MAO, and 1.04 mg of compound AT (1.0 ml of a 10.4 mg in 10 ml of toluene solution) were added to the reactor. The reactor was heated at 80° C., the ethylene was introduced (65 psi), and the reaction was allowed to run for 10 minutes, followed by rapidly cooling and venting the system. After evaporation of the toluene, 30.6 g of an ethylene-1-octene copolymer was recovered (MW=73,100, MWD=2.552, 77.7 SCB/1000C by $^{13}C$ NMR).

Example 48

Polymerization—Compound ST

Using the same reactor design and general procedure described in Example 40, 400 ml of toluene, 5.0 ml of 1.0 M MAO, and 0.248 mg of compound BT (0.2 ml of a 12.4 mg in 10 ml of toluene solution) were added to the reactor. The reactor was heated at 80° C., the ethylene was introduced (60 psi), and the reaction was allowed to run for 10 minutes, followed by rapidly cooling and venting the system. After evaporation of the toluene, 3.8 g of polyethylene was recovered (MW=451,400, MWD=3.692).

Example 49

Polymerization—Compound CT

Using the same reactor design and general procedure described in Example 40, 400 ml of toluene, 5.0 ml of 1.0 M MAO, and 0.234 mg of compound CT (0.2 ml of a 11.7 mg in 10 ml of toluene solution) were added to the reactor. The reactor was heated at 80° C., the ethylene was introduced (60 psi), and the reaction was allowed to run for 10 minutes, followed by rapidly cooling and venting the system. After evaporation of the toluene, 2.7 g of polyethylene was recovered (MW=529,100, MWD=3.665).

Example 50

Polymerization—Compound DT

Using the same reactor design and general procedure described in Example 40, 400 ml of toluene, 5.0 ml of 1.0

M MAO, and 0.28 mg of compound DT (0.2 ml of a 14.0 mg in 10 ml of toluene solution) were added to the reactor. The reactor was heated at 80° C., the ethylene was introduced (60 psi), and the reaction was allowed to run for 10 minutes, followed by rapidly cooling and venting the system. After evaporation of the toluene, 9.0 g of polyethylene was recovered (MW=427,800, MWD=3.306).

Example 51

Polymerization—Compound DT

Using the same reactor design and general procedure described in Example 40, 300 ml of toluene, 100 ml propylene, 7.0 ml of 1.0 M MAO, and 1.4 mg of compound DT (1.0 ml of a 14.0 mg in 10 ml of toluene solution) were added to the reactor. The reactor was heated at 30° C. and the reaction was allowed to run for 1 hour, followed by rapidly cooling and venting the system. After evaporation of the toluene, 15 g of amorphous polypropylene was recovered (MW=18,600, MWD=1.657).

Example 52

Polymerization—Compound ET

Using the same reactor design and general procedure described in Example 40, 300 ml of toluene, 100 ml 1-hexene, 70 ml of 1.0 M MAO, and 1.0 mg of compound ET (1.0 ml of a 10.0 mg in 10 ml of toluene solution) were added to the reactor. The reactor was heated at 80° C. and the ethylene was introduced (65 psi). During the polymerization, the reactor temperature increased by 20° C. After 10 minutes, the reactor was rapidly cooled and vented. After evaporation of the toluene, 106 g of an ethylene-1-hexene copolymer was recovered (MW=17,900, MWD=2.275, 39.1 SCB/1000C by NMR).

Example 53

Polymerization—Compound AT

The polymerization was performed in a stirred 100 ml stainless steel autoclave which was equipped to perform polymerizations at temperatures up to 300° C. and pressures up to 2500 bar. The reactor was evacuated, purged with nitrogen, purged with ethylene and heated to 200° C. 1-hexene (75 ml) was added to the reactor under ethylene pressure. A stock solution of compound AT was prepared by dissolving 6.5 mg of compound AT in 12.5 ml of toluene. The test solution was prepared by adding 1.0 ml of the compound AT stock solution to 1.9 ml of 1.0 M MAO solution, followed by 7.1 ml of toluene. The test solution (0.43 ml) was transferred by nitrogen pressure into a constant-volume injection tube. The autoclave was pressurized with ethylene to 1748 bar and was stirred at 1800 rpm. The test solution was injected into the autoclave with excess pressure, at which time a temperature rise of 16° C. was observed. The temperature and pressure were recorded continuously for 120 seconds, at which time the contents of the autoclave were rapidly vented into a receiving vessel. The reactor was washed with xylene to recover any polymer remaining within. These washings were combined with the polymer released when the reactor was vented. Precipitation of the polymer from the mixture by addition of acetone yielded 2.7 g of polymer (MW=64,000, MWD=3.16, 14.7 SCB/1000C by IR).

Example 54

Polymerization—Compound AT

For this Example a stirred 1 L steel autoclave reaction vessel which was equipped to perform continuous Ziegler polymerization reactions at pressures to 2500 bar and temperatures up to 300° C. was used. The reaction system was supplied with a thermocouple and pressure transducer to measure temperature and pressure continuously, and with means to supply continuously purified compressed ethylene and 1-butene (or propylene). Equipment for continuously introducing a measured flow of catalysts solution, and equipment for rapidly venting and quenching the reaction, and of collecting the polymer product were also a part of the reaction system. The polymerization was performed with a molar ratio of ethylene to 1-butene of 1.6 without the addition of a solvent. The temperature of the cleaned reactor containing ethylene and 1-butene was equilibrated at the desired reaction temperature of 180° C. The catalyst solution was prepared by mixing 0.888 g of solid compound AT with 0.67 L of a 30 wt % methylalumoxane solution in 4.3 L of toluene in an inert atmosphere. This catalyst solution was continuously fed by a high pressure pump into the reactor at a rate of 0.56 L/hr which resulted in a temperature of 180° C. in the reactor. During this run, ethylene and 1-butene were pressured into the autoclave at a total pressure of 1300 bar. The reactor contents were stirred at 1000 rpm. The yield of polymer products was 3.9 kg/hr of an ethylene-1-butene copolymer which had a weight average molecular weight of 50,200, a molecular weight distribution of 2.36 and 60.1 SCB/1000C as measured by $^{13}C$ NMR.

Example 55

Polymerization—Compound AT

Using the same reactor design as described in Example 54, and using a molar ratio of ethylene to propylene of 2.6 without the addition of a solvent. The temperature of a cleaned reactor containing ethylene and propylene was equilibrated at the desired reaction temperature of 140° C. The catalyst solution was prepared by mixing 0.779 g of solid compound AT with 0.5 L of a 30 wt % methylalumoxane solution in 24.5 L of toluene in an inert atmosphere. This catalyst solution was continuously fed by a high pressure pump into the reactor at a rate of 0.9 L/hr which resulted in a temperature of 140° C. in the reactor. During this run, ethylene and propylene were pressured into the autoclave at a total pressure of 2200 bar. The reactor contents were stirred at 1000 rpm. The yield of polymer product was 2.3 kg/hr of an ethylene-propylene copolymer which had a weight average molecular weight of 102,700, a molecular weight distribution of 2.208 and a density of 0.863 g/cc.

Example 56

Polymerization—Compound FT

Using the same reactor design as described in Example 54, and using a molar ratio of ethylene to 1-butene of 1.6 without the addition of a solvent. The temperature of the cleaned reactor containing ethylene and 1-butene was equilibrated at the desired reaction temperature of 180° C. The catalyst solution was prepared by mixing 0.859 g of solid FT with 30 wt % methylalumoxane solution and toluene such that the catalyst concentration was 0.162 g/L with an Al/M molar ratio of 1200. The preparation was done under an inert atmosphere. This catalyst solution was continuously fed by a high pressure pump into the reactor at a rate of 1.15 L/hr which resulted in a temperature of 180° C. in the reactor. During this run, ethylene and 1-butene were pressured into the autoclave at a total pressure of 1300. The reactor contents were stirred at 1000 rpm. The yield of polymer product was 3.9 kg/hr of an ethylene-1-butene copolymer which had a weight average molecular weight of 61,400, a molecular weight distribution of 2.607 and 104.8 SCB/1000C by $^{13}$C NMR.

Example 57

Polymerization—Compound GT

Using the same reactor design and general procedure as described in Example 40, 300 ml of toluene, 100 ml of 1-hexene, 7.0 ml of 1.0 M MAO, and 1.23 mg of compound GT (1.0 ml of a 12.3 mg in 10 ml of toluene solution) were added to the reactor. The reactor was heated at 80° C., and ethylene was introduced (65 psi), and the reaction was allowed to run for 30 minutes, followed by rapidly cooling and venting the system. After evaporation of the toluene, 47.2 g of an ethylene-1-hexene copolymer was recovered (MW=313,000, MWD=3.497, 41.0 SCB/1000C by $^{13}$C NMR.

Example 58

Polymerization—Compound AT

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 170° C. The catalyst solution was prepared by mixing 0.925 g of solid compound AT with 2 L of a 10 wt % methylalumoxane solution in 8 L of toluene in an inert atmosphere. This catalyst solution was continuously fed by a high pressure pump into the reactor at a rate of 0.28 L/hr which resulted in a temperature of 170° C. in the reactor. During this run, ethylene and 1-butene were pressured into the autoclave at a total pressure of 1300 bar. The reactor contents were stirred at 1000 rpm. The yield of polymer product was 3.7 kg/hr of an ethylene-1-butene copolymer which had a weight average molecular weight of 69,500, a molecular weight distribution of 2.049 and 35.7 SCB/1000C by $^{13}$C NMR.

Example 59

Polymerization—Compound BT

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 0.995 g of solid compound BT with 30 wt % methylalumoxane solution and toluene such that the catalyst concentration was 0.187 g/L and the Al/M molar ratio was 1300. The preparation was done under an inert atmosphere. This catalyst solution was continuously fed by a high pressure pump into the reactor at a rate of 1.0 L/hr which resulted in a temperature of 180° C. in, the reactor. During this run, ethylene and 1-butene were pressured into the autoclave at a total pressure of 1300 bar. The reactor contents were stirred at 1000 rpm. The yield of polymer product was 3.9 kg/hr of an ethylene-1-butene copolymer which had a weight average molecular weight of 65,000, a molecular weight distribution of 2.623 and 55.5 SCB/1000C as measured by $^{13}$C NMR.

Example 60

Polymerization—Compound H

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 1.94 g of solid compound H with 2.0 L of a 10 wt % methylalumoxane solution in 3 L of toluene in an inert atmosphere. This catalyst solution was continuously fed by a high pressure pump into the reactor at a rate of 1.5 L/hr which resulted in a temperature of 180° C. in the reactor. During this run, ethylene and 1-butene were pressured into the autoclave at a total pressure of 1300 bar. The reactor contents were stirred at 1000 rpm. The yield of polymer product was 3.9 kg/hr of an ethylene-1-butene copolymer which had a weight average molecular weight of 31,900 and 46.5 SCB/1000C as measured by $^{13}$C NMR.

Example 61

Polymerization—Compound I

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 1.92 g of solid compound I with 2.0 L of a 10 wt % methylalumoxane solution in 3 L of toluene in an inert atmosphere. This catalyst solution was continuously fed by a high pressure pump into the reactor at a rate of 0.67 L/hr which resulted in a temperature of 180° C. in the reactor. During this run, ethylene and 1-butene were pressured into the autoclave at a total pressure of 1300 bar. The reactor contents were stirred at 1000 rpm. The yield of polymer product was 3.9 kg/hr of an ethylene-1-butene copolymer which had a weight average molecular weight of 40,800, a molecular weight distribution of 2.009 and 36.9 SCB/1000C as measured by $^{13}$C NMR.

Example 62

Polymerization—Compound K

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 1.80 g of solid compound K with 2.0 L of a 10 wt % methylalumoxane solution in 3 L of toluene in an inert atmosphere. This catalyst solution was continuously fed by a high pressure pump into the reactor at a rate of 1.7 L/hr which resulted in a temperature of 180° C in the reactor. During this run, ethylene and 1-butene were pressured into the autoclave at a total pressure of 1300 bar. The reactor contents were stirred at 1000 rpm. The yield of polymer product was 3.9 kg/hr of an ethylene-1-butene copolymer which had a weight average molecular weight of 51,700, a molecular weight distribution of 1.532 and 30.1 SCB/1000C as measured by $^{13}$C NMR.

Example 63

Polymerization—Compound L

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 1.95 g of solid compound L with 2.0 L of a 10 wt % methylalumoxane solution in 3 L of toluene in an inert atmosphere. This catalyst solution was continuously fed by a high pressure pump into the reactor at a rate of 1.2 L/hr which resulted in a temperature of 180° C. in the reactor. During this run, ethylene and 1-butene were pressured into the autoclave at a total pressure of 1300 bar. The reactor contents were stirred at 1000 rpm. The yield of polymer product was 3.9 kg/hr of an ethylene-1-butene copolymer which had a weight average molecular weight of 38,800, a molecular weight distribution of 1.985 and 39.3 SCB/1000C as measured by $^{13}$C NMR.

Example 64

Polymerization—Compound HT

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 2.01 g of solid compound HT with 30 wt % methylalumoxane solution and toluene such that the catalyst concentration was 0.354 g/L and the Al/M molar ratio was 400. The preparation was done under an inert atmosphere. This catalyst solution was continuously fed by a high pressure pump into the reactor at a rate of 1.15 L/hr which resulted in a temperature of 180° C. in the reactor. During this run, ethylene and 1-butene were pressured into the autoclave at a total pressure of 1300 bar. The reactor contents were stirred at 1000 rpm. The yield of polymer porudct was 3.9 kg/hr of an ethylene-1-butene copolymer which had a weight average molecular weight of 61,700, a molecular weight distribution of 2.896 and 62.9 SCB/1000C as measured by $^{13}$C NMR.

Example 65

Polymerization—Compound F

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 1.31 g of solid compound F with 2.0 L of a 10 wt % methylalumoxane soution in 3 L of toluene in an inert atmosphere. This catalyst solution was continuously fed by a high pressure pump into the reactor at a rate of 0.56 L/hr which resulted in a temperature of 180° C in the reactor. During this run, ethylene and 1-butene were pressured into the atuoclave at a total pressure of 1300 bar. The reactor contents were stirred at 1000 rpm. The yield of polymer product was 3.9 kg/hr of an ethylene-1-butene copolymer which had a weight average molecular weight of 43,400, a molecular weight distribution of 2.001 and 40.1 SCB/1000C as measured by $^{13}$C NMR.

Example 66

Polymerization—Compound G

Using the same reactor design as described in Example 54, and using a molar ratio fo ethylene to 1-butene of 1.6 without the addition of a solvent, the temperature of the cleaned reactor containing ethylene and 1-butene was equilibrated at the desired reaction temperature of 180° C. The catalyst solution was prepared by mixing 1.53 g of solid compound G with 0.5 L of a 30 wt % methylalumoxane solution in 4.5 L of toluene in an inert atmosphere. This catalyst solution was continuously fed by a high pressure pump into the reactor at a rate of 0.58 L/hr which resulted in a temperature of 180° C. in the reactor. During this run, ethylene and 1-butene were pressured into the autoclave at a total pressure of 1300 bar. The reactor contents were stirred at 1000 rpm. The yield of polymer product was 3.9 kg/hr of an ethylene-1-butene copolymer which had a weight average molecular weight of 47,400, a molecular weight distribution of 2.198 and 37.6 SCB/1000C as measured by $^{13}$C NMR.

Example 67

Polymerization—Compound IT

Using the same reator design as described in Example 54, and using a molar ratio of ethylene to 1-butene of 1.6 without the addition of a solvent, the temperature of the cleaned reactor containing ethylene and 1-butene was equilibrated at the desired reaction temperature or 180° C. The catalyst solution was prepared by mixing 1.94 g of solid compound IT with 30 wt % methylalumoxane solution and toluene such that the catalyst concentration was 0.388 g/L and the Al/M molar ratio was 600. The preparation was done under an inert atmosphere. This catalyst soution was continuously fed by a high pressure pump into the reactor at a rate of 0.42 L/hr which resulted in a temperature of 180° C. in the reactor. During this run, ethylene and 1-butene were pressured into the autoclave at a total pressure of 1300 bar. The reactor contents were stirred at 1000 rpm. The yield of polymer porudct was 3.9 kg/hr of an ethylene-1-butene copolymer which had a weight average molecular weight of 50,800, a molecular weight distribution of 2.467 and 69 SCB/1000C as measured by $^1$H NMR.

Example 68

Polymerization—Compound A

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 1.95 g of solid compound A with 0.67 L of a 30 wt % methylalumoxane solution in 4.3 L of toluene in an inert atmosphere. This catalyst solution was continuously fed by a high pressure pump into the reactor at a rate of 0.4 L/hr which resulted in a temperature of 180° C. in the reactor. During this run, ethylene and 1-butene were pressured into the autoclave at a total pressure of 1300 bar. The reactor contents were stirred at 1000 rpm. The yield of polymer products was 3.9 kg/hr of an ethylene-1-butene copolymer which had a weight average molecular weight of 71,100, a molecular weight distribution of 1.801 and 12.4 SCB/1000C as measured by $^{13}$C NMR.

Example 69

Polymerization—Compound D

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 1.97 g of solid compound B with 0.67 L of a 30 wt % methylalumoxane solution in 4.3 L of toluene in an inert atmosphere. This catalyst solution was continuously fed by a high pressure pump into the reactor at a rate of 0.35 L/hr which resulted in a temperature of 180° C. in the reactor. During this run, ethylene and 1-butene were pressured into the autoclave at a total pressure of 1300 bar. The reactor contents were stirred at 1000 rpm. The yield of polymer product was 3.9 kg/hr of an ethylene-1-butene copolymer which has a weight average molecular weight of 47,300, and a molecular weight distribution of 2.056 and 34.1 SCB/1000C as measured by $^{13}$C NMR.

Example 70

Polymerization—Compound JT

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 1.78 g of solid compound JT with 30 wt % methylalumoxane solution and toluene such that the catalyst concentration was 0.318 g/L and the Al/M molar ratio was 1400. The preparation was done under an inert atmosphere. This catalyst solution was continuously fed by a high pressure pump into the reactor at a rate of 0.55 L/hr which resulted in a temperature of 180° C. in the reactor. During thus run, ethylene and 1-butene were pressured into the autoclave at a total pressure of 1300 bar. The reactor contents were stirred at 1000 rpm. The yield of polymer product was 3.9 kg/hr of an ethylene-1-butene copolymer which had a weight average molecular weight of 72,600, a molecular weight distribution of 2.385 and 110 SCB/1000C as measured by $^{1}$H NMR.

Table 2 summarizes the polymerization conditions employed and the properties obtained in the product polymers as set forth in Examples 1–39 above.

TABLE 2

| EXP. NO. | DILUENT Type | DILUENT ml | TRANSITION METAL COMPOUND (TMC) Type | TRANSITION METAL COMPOUND (TMC) mmole | ALUMOXANE Type | ALUMOXANE mmole | mmole MAO:TMC (×10³) | MONOMER | CO-MONOMER | RXN TEMP. °C. | RXN TIME HR. | YIELD g. | MW | MWD | SCB/1000 C NMR | SCB/1000 C IR | CAT. ACTIVITY G. POLYMER/MMOLE TMC-MOLE |
|---|---|---|---|---|---|---|---|---|---|---|---|---|---|---|---|---|---|
| 4 | Hexane | 300 | A | 5.588 × 10⁻⁴ | MAO | 9 | 16.11 | ethylene-60 psi | | 80 | 0.5 | 5.4 | 212,600 | 2.849 | | | 1.933 × 10⁴ |
| 1 | Toluene | 400 | A | 5.588 × 10⁻⁴ | MAO | 9 | 16.11 | ethylene-60 psi | | 80 | 0.5 | 9.2 | 257,200 | 2.275 | | | 3.293 × 10⁴ |
| 2 | Toluene | 300 | A | 2.794 × 10⁻⁴ | MAO | 4.5 | 16.11 | ethylene-60 psi | | 80 | 0.5 | 3.8 | 359,800 | 2.425 | | | 2.720 × 10⁴ |
| 3 | Toluene | 300 | A | 2.794 × 10⁻⁴ | MAO | 4.5 | 16.11 | ethylene-60 psi | | 40 | 0.5 | 2.4 | 635,000 | 3.445 | | | 1.718 × 10⁴ |
| 16 | Toluene | 400 | A | 5.588 × 10⁻⁴ | MAO | 5 | 8.95 | ethylene-400 psi | | 80 | 0.5 | 19.4 | 343,700 | 3.674 | | | 6.943 × 10⁴ |
| 12 | Toluene | 400 | Aᵃ | 5.588 × 10⁻⁴ | MAO | 5.02 | 8.98 | ethylene-60 psi | | 80 | 0.5 | 3.4 | 285,000 | 2.806 | | | 1.217 × 10⁴ |
| 13 | Toluene | 400 | Aᵃ,ᵇ | 5.588 × 10⁻⁴ | MAO | 5.02 | 8.98 | ethylene-60 psi | | 80 | 0.5 | 2.0 | 260,700 | 2.738 | | | 7.158 × 10³ |
| 14 | Toluene | 400 | Aᵃ | 5.588 × 10⁻⁴ | MAO | 0.26 | 0.47 | ethylene-60 psi | | 80 | 0.5 | 1.1 | 479,600 | 3.130 | | | 3.937 × 10³ |
| 15 | Toluene | 400 | Aᵃ | 5.588 × 10⁻⁴ | MAO | 0.1 | 0.018 | ethylene-60 psi | | 80 | 0.5 | 1.6 | 458,800 | 2.037 | | | 5.727 × 10² |
| 18 | Toluene | 400 | B | 5.573 × 10⁻⁴ | MAO | 5 | 8.97 | ethylene-60 psi | | 80 | 0.17 | 9.6 | 241,200 | 2.628 | | | 1.034 × 10⁵ |
| 19 | Toluene | 300 | C | 1.118 × 10⁻³ | MAO | 4 | 3.58 | ethylene-60 psi | | 80 | 0.5 | 1.1 | 278,400 | 2.142 | | | 3.041 × 10³ |
| 20 | Toluene | 400 | D | 5.573 × 10⁻⁴ | MAO | 5 | 8.97 | ethylene-60 psi | | 80 | 0.5 | 1.9 | 229,700 | 2.618 | | | 6.819 × 10³ |
| 21 | Hexane | 300 | E | 5.61 × 10⁻⁴ | MAO | 9 | 16.04 | ethylene-60 psi | | 80 | 0.5 | 2.2 | 258,200 | 2.348 | | | 7.843 × 10³ |
| 23 | Toluene | 400 | F | 4.79 × 10⁻⁴ | MAO | 5 | 10.44 | ethylene-60 psi | | 80 | 0.5 | 5.3 | 319,900 | 2.477 | | | 2.213 × 10⁴ |
| 25 | Toluene | 400 | G | 5.22 × 10⁻⁴ | MAO | 5 | 9.58 | ethylene-60 psi | | 80 | 0.5 | 3.5 | 237,300 | 2.549 | | | 1.341 × 10⁴ |
| 27 | Toluene | 400 | H | 5.62 × 10⁻⁴ | MAO | 5 | 8.90 | ethylene-60 psi | | 80 | 0.5 | 11.1 | 299,800 | 2.569 | | | 3.950 × 10⁴ |
| 29 | Toluene | 400 | I | 5.57 × 10⁻⁴ | MAO | 5 | 8.98 | ethylene-60 psi | | 80 | 0.5 | 0.9 | 377,000 | 1.996 | | | 3.232 × 10³ |
| 30 | Toluene | 400 | J | 5.59 × 10⁻⁴ | MAO | 5 | 8.94 | ethylene-60 psi | | 80 | 0.5 | 8.6 | 321,000 | 2.803 | | | 3.077 × 10⁴ |
| 32 | Toluene | 300 | K | 5.06 × 10⁻⁴ | MAO | 5 | 9.87 | ethylene-60 psi | | 80 | 0.5 | 26.6 | 187,300 | 2.401 | | | 1.051 × 10⁵ |
| 34 | Toluene | 400 | L | 5.60 × 10⁻⁴ | MAO | 5 | 8.93 | ethylene-60 psi | | 80 | 0.5 | 15.5 | 174,300 | 2.193 | | | 5.536 × 10⁴ |
| 5 | Toluene | 300 | A | 1.118 × 10⁻³ | MAO | 9 | 8.05 | ethylene-60 psi | propylene-200 ml | 80 | 0.5 | 13.3 | 24,900 | 2.027 | | 73.5 | 2.379 × 10⁴ |
| 6 | Toluene | 200 | A | 2.235 × 10⁻³ | MAO | 9 | 4.03 | ethylene-60 psi | propylene-200 ml | 50 | 0.5 | 6.0 | 83,100 | 2.370 | | 75.7 | 5.369 × 10³ |
| 7 | Toluene | 150 | A | 5.588 × 10⁻⁴ | MAO | 9 | 1.61 | ethylene-65 psi | 1-butene-100 ml | 50 | 0.5 | 25.4 | 184,500 | 3.424 | 23.5 | 21.5 | 9.091 × 10³ |

TABLE 2-continued

| EXP. NO. | DILUENT Type | ml | TRANSITION METAL COMPOUND (TMC) Type | mmole | ALUMOXANE Type | mmole | mmole MAO:TMC (×10³) | MONOMER | CO-MONOMER | RXN TEMP. °C. | RXN TIME HR. | YIELD g. | MW | MWD | NMR | SCB/1000 C IR | CAT. ACTIVITY G. POLYMER/MMOLE TMC-MOLE |
|---|---|---|---|---|---|---|---|---|---|---|---|---|---|---|---|---|---|
| 8 | Toluene | 100 | A | 5.588 × 10⁻³ | MAO | 9 | 1.61 | ethylene-65 psi | 1-butene-150 ml | 50 | 0.5 | 30.2 | 143,400 | 3.097 | 30.8 | 26.5 | 1.081 × 10⁴ |
| 9 | Toluene | 200 | A | 5.588 × 10⁻³ | MAO | 8 | 1.43 | ethylene-65 psi | 1-butene-50 ml | 50 | 0.5 | 24.9 | 163,200 | 3.290 | 23.3 | 18.9 | 8.912 × 10³ |
| 10 | Hexane | 200 | A | 5.588 × 10⁻³ | MAO | 8 | 1.43 | ethylene-65 psi | 1-butene-50 ml | 50 | 0.5 | 19.5 | 150,600 | 3.510 | 12.1 | 12.7 | 6.979 × 10³ |
| 11 | Hexane | 150 | A | 5.588 × 10⁻³ | MAO | 8 | 1.43 | ethylene-65 psi | 1-butene-50 ml | 50 | 0.5 | 16.0 | 116,200 | 3.158 | 19.2 | 19.4 | 5.727 × 10³ |
| 22 | Toluene | 200 | E | 5.61 × 10⁻³ | MAO | 9 | 1.60 | ethylene-65 psi | 1-butene-100 ml | 50 | 0.5 | 1.8 | 323,600 | 2.463 | | 33.5 | 6.417 × 10² |
| 24 | Toluene | 150 | F | 4.79 × 10⁻³ | MAO | 9 | 1.88 | ethylene-65 psi | 1-butene-100 ml | 50 | 0.5 | 3.5 | 251,300 | 3.341 | | 33.3 | 1.461 × 10³ |
| 26 | Toluene | 150 | G | 5.22 × 10⁻³ | MAO | 7 | 1.34 | ethylene-65 psi | 1-butene-100 ml | 50 | 0.5 | 7.0 | 425,000 | 2.816 | | 27.1 | 2.682 × 10³ |
| 28 | Toluene | 150 | H | 5.62 × 10⁻³ | MAO | 7 | 1.25 | ethylene-65 psi | 1-butene-100 ml | 50 | 0.5 | 15.4 | 286,600 | 2.980 | | 45.4 | 5.480 × 10³ |
| 30 | Toluene | 150 | J | 5.59 × 10⁻³ | MAO | 7 | 1.25 | ethylene-65 psi | 1-butene-100 ml | 50 | 0.5 | 11.2 | 224,800 | 2.512 | | 49.6 | 4.007 × 10³ |
| 32 | Toluene | 150 | K | 5.06 × 10⁻³ | MAO | 7 | 1.38 | ethylene-65 psi | 1-butene-100 ml | 50 | 0.5 | 3.9 | 207,600 | 2.394 | | 33.9 | 1.542 × 10³ |
| 35 | Toluene | 250 | A | 5.588 × 10⁻³ | MAO | 7 | 1.25 | ethylene-65 psi | 1-hexene-100 ml | 50 | 0.5 | 26.5 | 222,800 | 3.373 | | 39.1 | 9.485 × 10³ |
| 36 | Toluene | 300 | A | 5.588 × 10⁻³ | MAO | 7 | 1.25 | ethylene-65 psi | 1-octene-150 ml | 50 | 0.5 | 19.7 | 548,600 | 3.007 | | 16.5 | 6.979 × 10³ |
| 37 | Toluene | 300 | A | 5.588 × 10⁻³ | MAO | 7 | 1.25 | ethylene-65 psi | 4-methyl-1-pentene-100 ml | 50 | 0.5 | 15.1 | 611,800 | 1.683 | | 1.8ᶜ | 5.404 × 10³ |
| 38 | Toluene | 300 | A | 5.588 × 10⁻³ | MAO | 7 | 1.25 | ethylene-65 psi | norbornene-100 ml 2.2 M | 50 | 0.5 | 12.3 | 812,600 | 1.711 | | 0.3ᶜ | 4.402 × 10³ |
| 39 | Toluene | 300 | A | 5.588 × 10⁻³ | MAO | 7 | 1.25 | ethylene-65 psi | cis-1,4-hexadiene 100 ml | 50 | 0.5 | 13.6 | 163,400 | 2.388 | | 2.2ᶜ | 4.868 × 10³ |

ᵃCompound A was preactivated by dissolving the compound in solvent containing MAO.
ᵇPreincubation of activated compound A was for one day.
ᶜMole % comonomer.

Tables A, B, and C summarize the polymerization conditions employed and the properties obtained in the polymer products of Example Nos. 40–50, 52, 54–59, 64, 67 and 70 wherein a titanium species of Group IV B metal component is employed in the catalyst system.

Table D summarizes the condition employed and properties obtained in the polymer products produced by catalyst systems wherein each Group IV B metal is the species of a monocyclopentadienyl compound which is otherwise of identical structure except for the identity of the Group IV B metal itself.

TABLE A

| Example Number | Transition Metal Compound (TMC) Type | mmole | Methylalumoxane (MAO) mmole | mmole MAO:TMC (×10$^3$) | Ethylene Pressure (psi) | Rxn Temp. °C. | Rxn Time hr. | Yield g | MW | MWD | Cat Activity g poly/mmole TMC-HR |
|---|---|---|---|---|---|---|---|---|---|---|---|
| 41* | AT | 4.79 × 10$^{-4}$ | 5.01 | 10.5 | 60 | 80 | 0.5 | 14.5 | 406,100 | 2.486 | 6.05 × 10$^4$ |
| 40 | AT | 4.79 × 10$^{-4}$ | 5 | 10.4 | 60 | 80 | 0.5 | 11.5 | 279,700 | 2.676 | 4.93 × 10$^4$ |
| 50 | DT | 5.59 × 10$^{-4}$ | 5 | 8.94 | 60 | 80 | 0.166 | 9.0 | 427,800 | 3.306 | 9.70 × 10$^4$ |
| 48 | BT | 5.58 × 10$^{-4}$ | 5 | 8.96 | 60 | 80 | 0.166 | 3.8 | 451,400 | 3.692 | 4.10 × 10$^4$ |
| 49 | CT | 5.59 × 10$^{-4}$ | 5 | 8.94 | 60 | 80 | 0.166 | 2.7 | 529,100 | 3.665 | 2.91 × 10$^4$ |

*Transition metal compound was preactivated before polymerization by admixing it with a quantity of methylalumoxane sufficient to provide a MAO:TMC ratio of 20.9.

TABLE B

| Example Number | Transition Metal Compound (TMC) Type | mmole | Methyl alumoxane (MAO) mmole | mmole MAO:TMC (×10$^3$) | Ethylene Pressure (psi) | Co-monomer Amount | Rxn. Temp. °C. | Rxn. Time hr. | Yield g | MW | MWD | SCB/ 1000 C$^c$ | Cat g Poly/ mmole TMC-HR |
|---|---|---|---|---|---|---|---|---|---|---|---|---|---|
| 45 | AT | 4.79 × 10$^{-3}$ | 7 | 1.46 | 65 | Propylene: 100 ml | 80 | 0.166 | 46.0 | 110,200 | 5.489 | (Propylene)$^b$ 80 wt % | 5.79 × 1 |
| 46 | AT | 2.39 × 10$^{-3}$ | 7 | 2.93 | 65 | 1-Butene: 100 ml | 80 | 0.166 | 35.1 | 94,400 | 2.405 | 165 | 8.85 × 1 |
| 44 | AT | 2.39 × 10$^{-3}$ | 7 | 2.93 | 65 | 1-Hexene: 25 ml | 50 | 0.166 | 15.0 | 310,000 | 2.579 | 47.2 | 3.78 × 1 |
| 43 | AT | 2.39 × 10$^{-3}$ | 7 | 2.39 | 65 | 1-Hexene: 25 ml | 80 | 0.166 | 29.2 | 129,800 | 2.557 | 53.0 | 7.36 × 1 |
| 42 | AT | 2.39 × 10$^{-3}$ | 7 | 2.93 | 65 | 1-Hexene: 100 ml | 80 | 0.166 | 48.6 | 98,500 | 1.745 | 117 | 1.22 × 1 |
| 52 | ET | 2.76 × 10$^{-3}$ | 7 | 2.54 | 65 | 1-Hexene: 100 ml | 80$^d$ | 0.166 | 106 | 17,900 | 2.275 | 39.1 | 2.31 × 1 |
| 57 | GT | 2.81 × 10$^{-3}$ | 7 | 2.49 | 65 | 1-Hexene: 100 ml | 80 | 0.5 | 47.2 | 313,000 | 3.497 | 41.0 | 3.36 × 1 |
| 47 | AT | 2.42 × 10$^{-3}$ | 7 | 2.89 | 65 | 1-Octene: 100 ml | 80 | 0.166 | 30.6 | 73,100 | 2.552 | 77.7 | 7.62 × 1 |

$^b$Determined by IR
$^c$Determined by $^{13}$C NMR
$^d$During polymerization the reactor temperature increased by 20° C.

TABLE C

| Example Number | Transition Metal Compound (TMC) | AL: TMC | Catalyst TMC Feed Rate (mmole/hr) | Comonomer (Com) | Ethylene/ Com Mole Ratio | Rxn. Pressure (bar) | Rxn. Temp °C. | Yield (kg/hr) | MW | MWD | SCB/$^f$ 1000 C | Cat. Activity kg Polymer/ mmol TMC |
|---|---|---|---|---|---|---|---|---|---|---|---|---|
| 55$^e$ | AT | 1200 | 1.63 | Propylene | 2.6 | 2200 | 140 | 2.3 | 102,700 | 2.208 | 127.7 | 1.4 |
| 54 | AT | 1500 | 0.231 | 1-Butene | 1.6 | 1300 | 180 | 3.9 | 50,200 | 2.36 | 60.1 | 16.9 |
| 67 | IT | 600 | 0.442 | 1-Butene | 1.6 | 1300 | 180 | 3.9 | 50,800 | 2.467 | 69$^g$ | 8.8 |
| 64 | HT | 400 | 1.05 | 1-Butene | 1.6 | 1300 | 180 | 3.9 | 61,700 | 2.896 | 62.9 | 3.7 |
| 59 | BT | 1300 | 0.421 | 1-Butene | 1.4 | 1300 | 180 | 3.9 | 65,000 | 2.623 | 55.5 | 9.3 |
| 58 | AT | 1400 | 0.060 | 1-Butene | 1.6 | 1300 | 170 | 3.7 | 69,500 | 2.049 | 35.7 | 61.7 |
| 56 | FT | 1200 | 0.366 | 1-Butene | 1.6 | 1300 | 180 | 3.9 | 61,400 | 2.607 | 104.8 | 8.3 |
| 70 | JT | 1400 | 0.366 | 1-Butene | 1.6 | 1300 | 180 | 3.9 | 72,600 | 2.385 | 110$^g$ | 10.7 |

$^e$. The polymer product had a density of 0.863 g/cc.
$^f$. Excepted where otherwise indicated, determined by $^{13}$CNMR.
$^g$. Determined by $^1$H NMR.

TABLE D

| Example Number | Transition Metal Compound (TMC) | TM | Catalyst TMC Feal Rate mmole/hr | Cat. Activity[h] kg Polymer/ mmol TMC | MW | MWR | SCB/1000 C | r1 |
|---|---|---|---|---|---|---|---|---|
| 54 | AT | Ti | 0.23 | 17.0 | 50,200 | 2.360 | 60.1 | 10.1 |
| 60 | H | Zr | 1.23 | 3.2 | 31,900 | 12.070 | 46.6 | 14.1 |
| 61 | I | Hf | 0.42 | 9.3 | 40,800 | 2.009 | 36.9 | 18.4 |
| 59 | BT | Ti | 0.42 | 9.3 | 65,000 | 2.623 | 55.5 | 11.2 |
| 62 | K | Xr | 1.25 | 3.1 | 51,700 | 1.523 | 30.1 | 23.4 |
| 63 | L | Hf | 0.81 | 4.8 | 1.15 | 1.985 | 39.3 | 17.2 |
| 64 | HT | Ti | 1.05 | 3.7 | 61,700 | 2.896 | 62.9 | 9.5 |
| 65 | F | Zr | 0.34 | 11.5 | 43,400 | 2.001 | 40.1 | 16.8 |
| 66 | G | Hf | 0.34 | 11.5 | 47,400 | 2.198 | 37.6 | 18.1 |
| 67 | IT | Ti | 0.44 | 8.9 | 50,800 | 2.467 | 69 | 8.4 |
| 68 | A | Zr | 0.38 | 10.3 | 71,100 | 1.801 | 12.4 | 59.9 |
| 69 | B | Hf | 0.69 | 5.7 | 47,300 | 2.056 | 34.1 | 20.3 |

[h]Polymer yield was 3.90 kg/hr.

It may be seen that the requirement for the alumoxane component can be greatly diminished by premixing the catalyst with the alumoxane prior to initiation of the polymerization (see Examples 12 through 15).

By appropriate selection of (1) Group IV B transition metal component for use in the catalyst system; (2) the type and amount of alumoxane used; (3) the polymerization diluent type and volume; (4) reaction temperature; and (5) reaction pressure, one may tailor the product polymer to the weight average molecular weight value desired while still maintaining the molecular weight distribution to a value below about 4.0.

The preferred polymerization diluents for practice of the process of the invention are aromatic diluents, such as toluene, or alkanes, such as hexane.

From the above examples it appears that for a catalyst system wherein the group IV B transition metal component is a titanium species of the following structure:

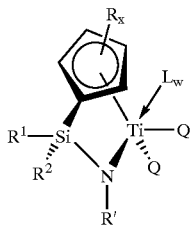

the nature of the R' group may dramatically influence the catalytic properties of the system. For production of ethylene-α-olein copolymers of greatest comonomer content, at a selected ethylene to α-olefin monomer ratio, R' is preferably a non-aromatic substituent, such as an alkyl or cycloalkyl substituent preferably bearing as primary or secondary carbon atom attached to the nitrogen atom.

Further, from the above data, the nature of the Cp ligand structure of a Ti metal component may be seen to influence the properties of the catalyst system. Those Cp ligands which are not too sterically hindered and which contain good electron donor groups, for example the $Me_4C_5$ ligand, are preferred.

The resins that are prepared in accordance with this invention can be used to make a variety of products including films and fibers.

The invention has been described with reference to its preferred embodiments. Those of ordinary skill in the art may, upon reading this disclosure, appreciate changes or modifications which do not depart from the scope and spirit of the invention as described above or claimed hereafter.

What is claimed is:

1. A process for producing a compound represented by the general formula:

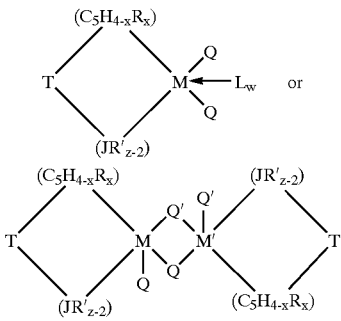

wherein M is Zr, Hf or Ti;

M' has the same meaning as M;

$(C_5H_{4-x}R_x)$ is a cyclopentadienyl ring which is substituted with from zero to four substituent groups R, "x" is 0, 1, 2, 3 or 4 denoting the degree of substitution, and each substituent group R is, independently, a radical selected from the group consisting of halogen radicals, $C_1$–$C_{20}$ hydrocarbyl radicals, substituted $C_1$–$C_{20}$ hydrocarbyl radicals where one or more hydrogen atoms is replaced by a halogen radical or $(C_5H_{4-x}R_x)$ is a cyclopentadienyl ring in which two adjacent R substituents are joined to form a ring to give an indenyl or tetrahydroindenyl ligand;

$(JR'_{z-2})$ is a heteroatom ligand in which J is an element with a coordination number of three from Group V A or an element with a coordination number of two from Group VI A of the Periodic Table of Elements, each R' is a radical selected from the group consisting of $C_1$–$C_{20}$ hydrocarbyl radicals, substituted $C_1$–$C_{20}$ hydrocarbyl radicals where one or more hydrogen atoms is replaced by a halogen radical, and "z" is the coordination number of the element J;

each Q is, independently, selected from the group consisting of hydride, methyl, ethyl, propyl, butyl, amyl, hexyl, heptyl, octyl, nonyl, decyl, cetyl, phenyl, chloro, bromo, fluoro, iodo, methoxy, ethoxy, propoxy, butoxy, phenoxy, methylphenoxy, dimethylamido, diethylamido, methylethylamido, dibutylamido, dipropylamido, diphenylamido, diphenylphosphido, dicyclohexylphosphido, diethylphosphido, and dimethylphosphido;

Q' has the same meaning as Q;

T is a covalent bridging group selected from the group consisting of dialkyl, alkylaryl or diaryl silicon or germanium radicals; and "L" is a neutral Lewis base where "w" denotes the number 0 or 1;

comprising reacting a Group IV B transition metal halide with a salt containing an anion of the formula $((C_5H_{4-x}R_x)\text{---}T\text{---}(JR'_{z-2}))^{-2}$ and either two cations from Group I A or one cation from Group II A of the Periodic Table of Elements.

2. A process for producing a compound represented by the general formula:

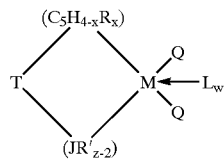

wherein M is Zr, Hf or Ti;

($C_5H_{4-x}R_x$) is a cyclopentadienyl ring which is substituted with from zero to four substituent groups R, "x" is 0, 1, 2, 3 or 4 denoting the degree of substitution, and each substituent group R is, independently, a radical selected from the group consisting of halogen radicals, $C_1$–$C_{20}$ hydrocarbyl radicals, substituted $C_1$–$C_{20}$ hydrocarbyl radicals where one or more hydrogen atoms is replaced by a halogen radical or ($C_5H_{4-x}R_x$) is a cyclopentadienyl ring in which two adjacent R substituents are joined to form a ring to give an indenyl or tetrahydroindenyl ligand;

($JR'_{z-2}$) is a heteroatom ligand in which J is an element with a coordination number of three from Group V A or an element with a coordination number of two from Group VI A of the Periodic Table of Elements, each R' is a radical selected from the group consisting Of $C_1$–$C_{20}$ hydrocarbyl radicals, substituted $C_1$–$C_{20}$ hydrocarbyl radicals where one or more hydrogen atoms is replaced by a halogen radical, and "z" is the coordination number of the element J;

each Q is, independently, selected from the group consisting of hydride, methyl, ethyl, propyl, butyl, amyl, hexyl, heptyl, octyl, nonyl, decyl, cetyl, phenyl, chloro, bromo, fluoro, iodo, methoxy, ethoxy, propoxy, butoxy, phenoxy, methylphenoxy, dimethylamido, diethylamido, methylethylamido, dibutylamido, dipropylamido, diphenylamido, diphenylphosphido, dicyclohexylphosphido, diethylphosphido, and dimethylphosphido;

T is a covalent bridging group selected from the group consisting of dimethylsilyl, diethylsilyl, di-n-propylsilyl, diisopropylsilyl, di-n-butylsilyl, di-t-butylsilyl, di-n-hexylsityl, methylphenylsilyl, ethylmethylsityl, diphenylsilyl, n-hexylmethylsilyl, cyclopentamethylenesilyl, cyclotetramethylenesilyl, cyclotrimethylenesilyl, dimethylgermyl and diethylgermyl; and "L" is a neutral Lewis base where "w" denotes the number 0 or 1;

comprising reacting a $d^0$ Group IV B transition metal halide with a salt containing an anion of the formula $((C_5H_{4-x}R_x)\text{---}T\text{---}(JR'_{z-2}))^{-2}$ and either two cations from Group I A or one cation from Group II A of the Periodic Table of Elements.

3. A process for producing a compound represented by the general formula:

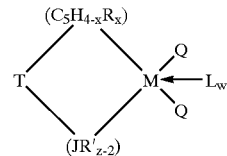

wherein M is Zr, Hf or Ti;

($C_5H_{4-x}R_x$) is a cyclopentadienyl ring which is substituted with from zero to four substituent groups R, "x" is 0, 1, 2, 3 or 4 denoting the degree of substitution, and each substituent group R is, independently, a radical selected from the group consisting of halogen radicals, $C_1$–$C_{20}$ hydrocarbyl radicals, substituted $C_1$–$C_{20}$ hydrocarbyl radicals where one or more hydrogen atoms is replaced by a halogen radical or ($C_5H_{4-x}R_x$) is a cyclopentadienyl ring in which two adjacent R substituents are joined to form a ring to give an indenyl or tetrahydroindenyl ligand;

($JR'_{z-2}$) is a heteroatom ligand in which J is an element with a coordination number of three from Group V A or an element with a coordination number of two from Group VI A of the Periodic Table of Elements, each R' is a radical selected from the group consisting of $C_1$–$C_{20}$ hydrocarbyl radicals, substituted $C_1$–$C_{20}$ hydrocarbyl radicals where one or more hydrogen atoms is replaced by a halogen radical, and "z" is the coordination number of the element J;

each Q is, independently, selected from the group consisting of hydride, methyl, ethyl, propyl, butyl, amyl, hexyl, heptyl, octyl, nonyl, decyl, cetyl, phenyl, chloro, bromo, fluoro, iodo, methoxy, ethoxy, propoxy, butoxy, phenoxy, methylphenoxy, dimethylamido, diethylamido, methylethylamido, dibutylamido, dipropylamido, diphenylamido, diphenylphosphido, dicyclohexylphosphido, diethylphosphido, and dimethylphosphido;

T is a covalent bridging group selected from the group consisting of methylene, dimethylmethylene, diethylmethylene, ethylene, dimethylethylene, diethylethylene and dipropylethylene;

"L" is a neutral Lewis base where "w" denotes the number 0 or 1;

comprising reacting a $d^0$ Group IV B transition metal halide with a salt containing an anion of the formula $((C_5H_{4-x}R_x)\text{---}T\text{---}(JR'_{z-2}))^{-2}$ and either two cations from Group I A or one cation from Group II A of the Periodic Table of Elements.

4. A process for producing a compound represented by the general formula:

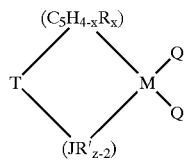

wherein M is Zr, Hf or Ti;

($C_5H_{4-x}R_x$) is a cyclopentadienyl ring which is substituted with from zero to four substituent groups R, "x" is 0, 1, 2, 3 or 4 denoting the degree of substitution, and each substituent group R is, independently, a radical selected from the group consisting of methyl, ethyl, propyl, butyl, octyl, benzyl, phenyl, trimethylgermyl, trimethylstannyl, triethylplumbyl, triflouromethyl, trimethylsilyl, triethylsilyl, ethyldimethylsilyl, methyldiethylsilyl, and triphenylgermyl, or ($C_5H_{4-x}R_x$) is a cyclopentadienyl ring in which two adjacent R substituents are joined to form a ring to give an indenyl or tetrahydroindenyl ligand;

($JR'_{z-2}$) is a heteroatom ligand selected from the group consisting of t-butylamido, phenylamido, p-n-butylphenylamido, cyclohexylamido, perfluorophenylamido, n-butylamido, methylamido, ethylamido, n-propylamido, isopropylamido, benzylamido, t-butylphosphido, ethylphosphido, phenylphosphido and cyclohexylphosphido, and "z" is 3;

each Q is, independently, selected from the group consisting of hydride, methyl, ethyl, propyl, butyl, amyl, hexyl, heptyl, octyl, nonyl, decyl, cetyl, phenyl, chloro, bromo, fluoro, iodo, methoxy, ethoxy, propoxy, butoxy, phenoxy, methylphenoxy, dimethylamido, diethylamido, methylethylamido, dibutylamido, dipropylamido, diphenylamido, diphenylphosphido, dicyclohexylphosphido, diethylphosphido, and dimethylphosphido;

T is a covalent bridging group selected from the group consisting of dimethylsilyl, diethylsilyl, di-n-propylsilyl, diisopropylsilyl, di-n-butylsilyl, di-t-butylsilyl, di-n-hexylsilyl, methylphenylsilyl, ethylmethylsilyl, diphenylsilyl, n-hexylmethylsilyl, cyclopentamethylenesilyl, cyclotetramethylenesilyl, cyclotrimethylenesilyl, dimethylgermyl and diethylgermyl; and comprising the step of reacting a $d^0$ Group IV B transition metal halide with a salt containing an anion of the formula $((C_5H_{4-x}R_x)-T-(JR'_{z-2}))^{-2}$ and either two cations from Group I A or one cation from Group II A of the Periodic Table of Elements.

5. A process for producing a compound represented by the general formula:

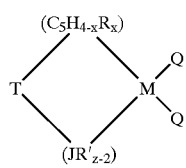

wherein M is Zr, Hf or Ti;

($C_5H_{4-x}R_x$) is a cyclopentadienyl ring which is substituted with from zero to four substituent groups R, "x" is 0, 1, 2, 3 or 4 denoting the degree of substitution, and each substituent group R is, independently, a radical selected from the group consisting of methyl, ethyl, propyl, butyl, octyl, benzyl, phenyl, triphenylgermyl, trimethylstannyl, triethylplumbyl, triflouromethyl, trimethylsilyl, triethylsilyl, ethypdimethylsilyl, methyldiethylsilyl, and triphenylgermyl, or ($C_5H_{4-x}R_x$) is a cyclopentadienyl ring in which two adjacent R substituents are joined to form a ring to give an indenyl or tetrahydroindenyl ligand;

($JR'_{z-2}$) is a heteroatom ligand selected from the group consisting of t-butylamido, phenylamido, p-n-butylphenylamido, cyclohexylamido, perfluorophenylamido, n-butylamido, methylamido, ethylamido, n-propylamido, isopropylamido, benzylamido, t-butylphosphido, ethyliphosphido, phenylphosphido and cyclohexylphosphido, and "z" is 3;

each Q is, independently, selected from the group consisting of hydride, methyl, ethyl, propyl, butyl, amyl, hexyl, heptyl, octyl, noneyl, decyl, cetyl, phenyl, chloro, bromo, fluoro, iodo, methoxy, ethoxy, propoxy, butoxy, phenoxy, methylphenoxy, dimethylamido, diethylamido, methylethylamido, dibutylamido, dipropylamido, diphenylamido, diphenylphosphido, dicyclohexylphosphido, diethylphosphido, and dimethylphosphido;

T is a covalent bridging group selected from the group consisting of methylene, dimethylmethylene, diethylmethylene, ethylene, dimethylethylene, diethylethylene and dipropylethylene;

comprising the steps of reacting a $d^0$ Group IV B transition metal halide with a salt containing an anion of the formula $((C_5H_{4-x}R_x)-T-(JR'_{z-2}))^{-2}$ and either two cations from Group I A or one cation from Group II A of the Periodic Table of Elements.

6. A process for producing a compound represented by the general formula:

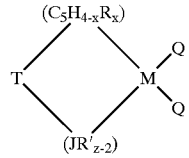

wherein M is Zr, Hf or Ti;

($C_5H_{4-x}R_x$) is a cyclopentadienyl ring which is substituted with from zero to four substituent groups R, "x" is 0, 1, 2, 3 or 4 denoting the degree of substitution, and each substituent group R is, independently, a radical selected from the group consisting of methyl, ethyl, propyl, butyl, octyl, benzyl, phenyl, trimethylgermyl, trimethylstannyl, triethylplumbyl, triflouromethyl, trimethylsilyl, triethylsilyl, ethyldimethylsilyl, methyldiethylsilyl, and triphenylgermyl, or ($C_5H_{4-x}R_x$) is a cyclopentadienyl ring in which two adjacent R substituents are joined to form a ring to give an indenyl or tetrahydroindenyl ligand;

($JR'_{z-2}$) is a heteroatom ligand selected from the group consisting of t-butylamido, phenylamido, p-n-butylphenylamido, cyclohexylamido, perfluorophenylamido, n-butylamido, methylamido, ethylamido, n-propylamido, isopropylamido, benzylamido, t-butylphosphido, ethylphosphido, phenylphosphido and cyclohexylphosphido, and "z" is 3;

each Q is, independently, selected from the group consisting of hydride, methyl, ethyl, propyl, butyl, amyl, hexyl, heptyl, octyl, nonyl, decyl, cetyl, phenyl, chloro, bromo, fluoro, iodo, methoxy, ethoxy, propoxy, butoxy, phenoxy, methylphenoxy, dimethylamido, diethylamido, methylethylamido, dibutylamido, dipropylamido, diphenylamido, diphenylphosphido, dicyclohexylphosphido, diethylphosphido, and dimethylphosphido;

T is a covalent bridging group selected from the group consisting of dimethylsilyl, diethylsilyl, di-n-propylsilyl, diisopropylsilyl, di-n-butylsilyl, di-t-butylsilyl, di-n-hexylsilyl, methylphenylsilyl, ethylmethylsilyl, diphenylsilyl, n-hexylmethylsilyl, cyclopentamethylenesilyl, cyclotetramethylenesilyl, cyclotrimethylenesilyl, dimethylgermyl, diethylgermyl, methylene, dimethylmethylene, diethylmethylene, ethylene, dimethylethylene, diethylethylene and dipropylethylene;

comprising reacting a $d^0$ Group IV B transition metal halide with a salt containing an anion of the formula $((C_5H_{4-x}R_x)-T-(JR'_{z-2}))^{-2}$ and either two cations from Group I A or one cation from Group II A of the Periodic Table of Elements in a solvent that is either pentane or 30–60 petroleum ether.

7. A process for producing a compound represented by the general formula:

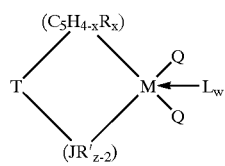

wherein M is Zr, Hf or Ti;

($C_5H_{4-x}R_x$) is a cyclopentadienyl ring which is substituted with from zero to four substituent groups R, "x" is 0, 1, 2, 3 or 4 denoting the degree of substitution, and each substituent group R is, independently, a radical selected from the group consisting of methyl, ethyl, propyl, butyl, octyl, benzyl, phenyl, trimethylgermyl, trimethylstannyl, triethylplumbyl, triflouromethyl, trimethylsilyl, triethylsilyl, ethyldimethylsilyl, methyldiethylsilyl, and triphenylgermyl, or ($C_5H_{4-x}R_x$) is a cyclopentadienyl ring in which two adjacent R substituents are joined to form a ring to give an indenyl or tetrahydroindenyl ligand;

($JR'_{z-2}$) is a heteroatom ligand selected from the group consisting of t-butylamido, phenylamido, p-n-butylphenylamido, cyclohexylamido, perfluorophenylamido, n-butylamido, methylamido, ethylamido, n-propylamido, isopropylamido, benzylamido, t-butylphosphido, ethylphosphido, phenylphosphido and cyclohexylphosphido, and "z" is 3;

each Q is, independently, selected from the group consisting of hydride, methyl, ethyl, propyl, butyl, amyl, hexyl, heptyl, octyl, nonyl, decyl, cetyl, phenyl, chloro, bromo, fluoro, iodo, methoxy, ethoxy, propoxy, butoxy, phenoxy, methylphenoxy, dimethylamido, diethylamido, methylethylamido, dibutylamido, dipropylamido, diphenylamido, diphenylphosphido, dicyclohexylphosphido, diethylphosphido, and dimethylphosphido;

T is a covalent bridging group selected from the group consisting of dimethylsilyl, diethylsilyl, di-n-propylsilyl, diisopropylsilyl, di-n-butylsilyl, di-t-butylsilyl, di-n-hexylsilyl, methylphenylsilyl, ethylmethylsilyl, diphenylsilyl, n-hexylmethylsilyl, cyclopentamethylenesilyl, cyclotetramethylenesilyl, cyclotrimethylenesilyl, dimethylgermyl, diethylgermyl, methylene, dimethylmethylene, diethylmethylene, ethylene, dimethylethylene, diethylethylene and dipropylethylene;

"L" is a neutral Lewis base where "w" denotes the number 0 or 1;

comprising reacting a $d^0$ Group IV B transition metal halide with a salt containing an anion of the formula $((C_5H_{4-x}R_x)-T-(JR'_{z-2}))^{-2}$ and either two cations from Group I A or one cation from Group II A of the Periodic Table of Elements in a solvent that is diethylether.

8. A process for producing a compound represented by the general formula:

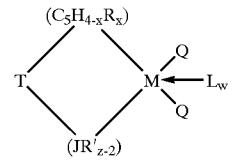

wherein M is Zr, Hf or Ti;

($C_5H_{4-x}R_x$) is a cyclopentadienyl ring which is substituted with from zero to four substituent groups R, "x" is 0, 1, 2, 3 or 4 denoting the degree of substitution, and each substituent group R is, independently, a radical selected from the group consisting of methyl, ethyl, propyl, butyl, octyl, benzyl, phenyl, trimethylgermyl, trimethylstannyl, triethylplumbyl, triflouromethyl, trimethylsilyl, triethylsilyl, ethyldimethylsilyl, methyldiethylsilyl, and triphenylgermyl, or ($C_5H_{4-x}R_x$) is a cyclopentadienyl ring in which two adjacent R substituents are joined to form a ring to give an indenyl or tetrahydroindenyl ligand;

($JR'_{z-2}$) is a heteroatom ligand selected from the group consisting of t-butylamido, phenylamido, p-n-butylphenylamido, cyclohexylamido, perfluorophenylamido, n-butylamido, methylamido, ethylamido, n-propylamido, isopropylamido, benzylamido, t-butylphosphido, ethylphosphido, phenylphosphido and cyclohexylphosphido, and "z" is 3;

each Q is, independently, selected from the group consisting of hydride, methyl, ethyl, propyl, butyl, amyl, hexyl, heptyl, octyl, nonyl, decyl, cetyl, phenyl, chloro, bromo, fluoro, iodo, methoxy, ethoxy, propoxy, butoxy, phenoxy, methylphenoxy, dimethylamido, diethylamido, methylethylamido, dibutylamido, dipropylamido, diphenylamido, diphenylphosphido, dicyclohexylphosphido, diethylphosphido, and dimethylphosphido;

T is a covalent bridging group selected from the group consisting of dimethylsilyl, diethylsilyl, di-n-propylsilyl, diisopropylsilyl, di-n-butylsilyl, di-t-butylsilyl, di-n-hexylsilyl, methylphenylsilyl, ethylmethylsilyl, diphenylsilyl, n-hexylmethylsilyl, cyclopentamethylenesilyl, cyclotetramethylenesilyl, cyclotrimethylenesilyl, dimethylgermyl, diethylgermyl, methylene, dimethylmethylene, diethylmethylene, ethylene, dimethylethylene, diethylethylene and dipropylethylene;

"L" is a neutral Lewis base where "w" denotes the number 0 or 1;

comprising the steps of reacting a $d^0$ Group IV B transition metal halide with a salt containing an anion of the formula $((C_5H_{4-x}R_x)\mathrm{-T-}(JR'_{z-2}))^{-2}$ and either two cations from Group I A or one cation from Group II A of the Periodic Table of Elements and adding methylene chloride to the product of the reacting step.

9. A process for producing a compound represented by the general formula:

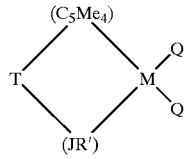

wherein:

M is Zr, Hf or Ti;

$(C_5Me_4)$ is a tetramethylcyclopentadienyl ring;

(JR') is a ligand in which J is nitrogen and R' is a tert-butyl radical;

each Q is chloro;

T is dimethylsilyl;

the step of the process comprising reacting $MCl_4$, where M is as previously defined, with a salt represented by the formula $Li_2((C_5Me_4)\mathrm{-Me_2Si\text{-}(N\text{-}t\text{-}butyl)})$.

10. A process for producing a compound represented by the general formula:

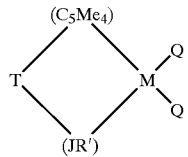

wherein:

M is Zr, Hf or Ti;

$(C_5Me_4)$ is a tetramethylcyclopentadienyl ring;

(JR') is a ligand in which J is nitrogen and R' is a cyclic aliphatic hydrocarbyl radical having up to 20 carbon atoms;

each Q is chloro;

T is dimethylsilyl;

the step of the process comprising reacting $MCl_4$, where M is as previously defined, with a salt represented by the formula $Li_2((C_5Me_4)\mathrm{-Me_2Si-(NR')})$, where R' is as previously defined.

11. The process of producing dimethylsilyl(tetramethylcyclopentadienyl)(t-butylamido)zirconium dichloride by reacting dilithium(dimethylsilyl(tetramethylcyclopentadienyl) (t-butylamido)) with zirconium tetrachloride.

12. A process for producing a compound represented by the general formula:

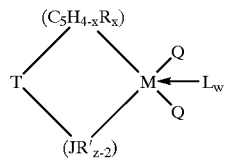

wherein M is Zr, Hf or Ti;

$(C_5H_{4-x}R_x)$ is a cyclopentadienyl ring which is substituted with from zero to four substituent groups R, "x" is 0, 1, 2, 3 or 4 denoting the degree of substitution, and each substituent group R is, independently, a radical selected from the group consisting of methyl, ethyl, propyl, butyl, octyl, benzyl, phenyl, trimethylgermyl, trimethylstannyl, triethylplumbyl, triflouromethyl, trimethylsilyl, triethylsilyl, ethyldimethylsilyl, methyldiethylsilyl, and triphenylgermyl, or $(C_5H_{4-x}R_x)$ is a cyclopentadienyl ring in which two adjacent R substituents are joined to form a ring to give an indenyl or tetrahydroindenyl ligand;

$(JR'_{z-2})$ is a heteroatom ligand in which J is an element with a coordination number of three from Group V A or an element with a coordination number of two from Group VI A of the Periodic Table of Elements, each R' is a radical selected from the group consisting of $C_1$–$C_{20}$ hydrocarbyl radicals and substituted $C_1$–$C_{20}$ hydrocarbyl radicals where one or more hydrogen atoms is replaced by a halogen radical, and "z" is the coordination number of the element J;

each Q is, independently, selected from the group consisting of hydride, methyl, ethyl, propyl, butyl, amyl, hexyl, heptyl, octyl, nonyl, decyl, cetyl, phenyl, chloro, bromo, fluoro, iodo, methoxy, ethoxy, propoxy, butoxy, phenoxy, methylphenoxy, dimethylamido, diethylamido, methylethylamido, dibutylamido, dipropylamido, diphenylamido, diphenylphosphido, dicyclohexylphosphido, diethylphosphido, and dimethylphosphido;

T is a covalent bridging group selected from the group consisting of dialkyl, alkylaryl or diaryl silicon or germanium radicals; and "L" is a neutral Lewis base where "w" denotes the number 0 or 1;

comprising reacting a $d^0$ Group IV B transition metal halide with a salt containing an anion of the formula $((C_5H_{4-x}R_x)\mathrm{-T-}(JR'_{z-2}))^{-2}$ and either two cations from Group I A or one cation from Group II A of the Periodic Table of Elements.

13. A process for producing a compound represented by the general formula:

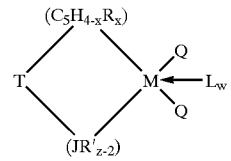

wherein M is Zr, Hf or Ti;

$(C_5H_{4-x}R_x)$ is a cyclopentadienyl ring which is substituted with from zero to four substituent groups R, "x" is 0, 1, 2, 3 or 4 denoting the degree of substitution, and each substituent group R is, independently, a radical selected from the group consisting of halogen radicals, $C_1$–$C_{20}$ hydrocarbyl radicals, substituted $C_1$–$C_{20}$ hydrocarbyl radicals where one or more hydrogen atoms is replaced by a halogen radical or $(C_5H_{4-x}R_x)$ is a cyclopentadienyl ring in which two adjacent R substituents are joined to form a ring to give an indenyl or tetrahydroindenyl ligand;

$(JR'_{z-2})$ is a heteroatom ligand in which J is an element with a coordination number of three from Group V A or an element with a coordination number of two from Group VI A of the Periodic Table of Elements, each R' is a radical selected from the group consisting of $C_1$–$C_{20}$ hydrocarbyl radicals and substituted $C_1$–$C_{20}$ hydrocarbyl radicals where one or more hydrogen atoms is replaced by a halogen radical, and "z" is the coordination number of the element J;

each Q is, independently, selected from the group consisting of hydride, methyl, ethyl, propyl, butyl, amyl, hexyl, heptyl, octyl, nonyl, decyl, cetyl, phenyl, chloro, bromo, fluoro, iodo, methoxy, ethoxy, propoxy, butoxy, phenoxy, methylphenoxy, dimethylamido, diethylamido, methylethylamido, dibutylamido, dipropylamido, diphenylamido, diphenylphosphido, dicyclohexylphosphido, diethylphosphido, and dimethylphosphido;

T is a covalent bridging group selected from the group consisting of dimethylsilyl, diethylsilyl, di-n-propylsilyl, diisopropylsilyl, di-n-butylsilyl, di-t-butylsilyl, di-n-hexylsilyl, methylphenylsilyl, ethylmethylsilyl, diphenylsilyl, n-hexylmethylsilyl, cyclopentamethylenesilyl, cyclotetramethylenesilyl, cyclotrimethylenesilyl, dimethylgermyl, diethylgermyl, methylene, dimethylmethylene, diethylmethylene, ethylene, dimethylethylene, diethylethylene and dipropylethylene; and "L" is a neutral Lewis base where "w" denotes the number 0 or 1;

comprising reacting a $d^0$ Group IV B transition metal halide with a salt containing an anion of the formula $((C_5H_{4-x}R_x)-T-(JR'_{z-2}))^{-2}$ and either two cations from Group I A or one cation from Group II A of the Periodic Table of Elements.

14. A process for producing a compound represented by the general formula:

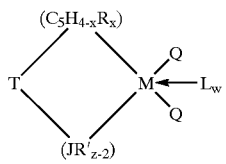

wherein M is Zr, Hf or Ti;

($C_5H_{4-x}R_x$) is a cyclopentadienyl ring which is substituted with from zero to four substituent groups R, "x" is 0, 1, 2, 3 or 4 denoting the degree of substitution, and each substituent group R is, independently, a radical selected from the group consisting of methyl, ethyl, propyl, butyl, octyl, benzyl, phenyl, trimethylgermyl, trimethylstannyl, triethylplumbyl, triflouromethyl, trimethylsilyl, triethylsilyl, ethyldimethylsilyl, methyldiethylsilyl, and triphenylgermyl, or ($C_5H_{4-x}R_x$) is a cyclopentadienyl ring in which two adjacent R substituents are joined to form a ring to give an indenyl or tetrahydroindenyl ligand;

($JR'_{z-2}$) is a heteroatom ligand in which J is an element with a coordination number of three from Group V A or an element with a coordination number of two from Group VI A of the Periodic Table of Elements, each R' is a radical selected from the group consisting of $C_1$–$C_{20}$ hydrocarbyl radicals and substituted $C_1$–$C_{20}$ hydrocarbyl radicals where one or more hydrogen atoms is replaced by a halogen radical, and "z" is the coordination number of the element J;

each Q is, independently, selected from the group consisting of hydride, methyl, ethyl, propyl, butyl, amyl, hexyl, heptyl, octyl, nonyl, decyl, cetyl, phenyl, chloro, bromo, fluoro, iodo, methoxy, ethoxy, propoxy, butoxy, phenoxy, methylphenoxy, dimethylamido, diethylamido, methylethylamido, dibutylamido, dipropylamido, diphenylamido, diphenylphosphido, dicyclohexylphosphido, diethylphosphido, and dimethylphosphido;

T is a covalent bridging group selected from the group consisting of dimethylsilyl, diethylsilyl, di-n-propylsilyl, diisopropylsilyl, di-n-butylsilyl, di-t-butylsilyl, di-n-hexylsilyl, methylphenylsilyl, ethylmethylsilyl, diphenylsilyl, n-hexylmethylsilyl, cyclopentamethylenesilyl, cyclotetramethylenesilyl, cyclotrimethylenesilyl, dimethylgermyl, diethylgermyl, methylene, dimethylmethylene, diethylmethylene, ethylene, dimethylethylene, diethylethylene and dipropylethylene; and "L" is a neutral Lewis base where "w" denotes the number 0 or 1;

comprising reacting a $d^0$ Group IV B transition metal halide with a salt containing an anion of the formula $((C_5H_{4-x}R_x)-T-(JR'_{z-2}))^{-2}$ and either two cations from Group I A or one cation from Group II A of the Periodic Table of Elements.

15. A process for producing a compound represented by the general formula:

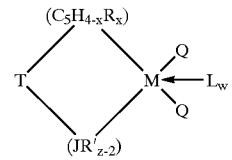

wherein M is Zr, Hf or Ti;

($C_5H_{4-x}R_x$) is a cyclopentadienyl ring which is substituted with from zero to four substituent groups R, "x" is 0, 1, 2, 3 or 4 denoting the degree of substitution, and each substituent group R is, independently, a radical selected from the group consisting of halogen radicals, $C_1$–$C_{20}$ hydrocarbyl radicals, substituted $C_1$–$C_{20}$ hydrocarbyl radicals where one or more hydrogen atoms is replaced by a halogen radical or ($C_5H_{4-x}R_x$) is a cyclopentadienyl ring in which two adjacent R substituents are joined to form a ring to give an indenyl or tetrahydroindenyl ligand;

($JR'_{z-2}$) is a heteroatom ligand selected from the group consisting of t-butylamido, phenylamido, p-n-butylphenylamido, cyclohexylamido, perfluorophenylamido, n-butylamido, methylamido, ethylamido, n-propylamido, isopropylamido, benzylamido, t-butylphosphido, ethylphosphido, phenylphosphido and cyclohexylphosphido, and "z" is 3;

each Q is, independently, selected from the group consisting of hydride, methyl, ethyl, propyl, butyl, amyl, hexyl, heptyl, octyl, nonyl, decyl, cetyl, phenyl, chloro, bromo, fluoro, iodo, methoxy, ethoxy, propoxy, butoxy, phenoxy, methylphenoxy, dimethylamido, diethylamido, methylethylamido, dibutylamido, dipropylamido, diphenylamido, diphenylphosphido, dicyclohexylphosphido, diethylphosphido, and dimethylphosphido;

T is a covalent bridging group selected from the group consisting of dialkyl, alkylaryl or diaryl silicon or germanium radicals; and "L" is a neutral Lewis base where "w" denotes the number 0 or 1;

comprising reacting a $d^0$ Group IV B transition metal halide with a salt containing an anion of the formula $((C_5H_{4-x}R_x)-T-(JR'_{z-2}))^{-2}$ and either two cations from Group I A or one cation from Group II A of the Periodic Table of Elements.

16. A process for producing a compound represented by the general formula:

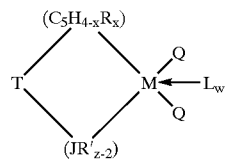

wherein M is Zr, Hf or Ti;

$(C_5H_{4-x}R_x)$ is a cyclopentadienyl ring which is substituted with from zero to four substituent groups R, "x" is 0, 1, 2, 3 or 4 denoting the degree of substitution, and each substituent group R is, independently, a radical selected from the group consisting of methyl, ethyl, propyl, butyl, octyl, benzyl, phenyl, trimethylgermyl, trimethylstannyl, triethylplumbyl, triflouromethyl, trimethylsilyl, triethylsilyl, ethyldimethylsilyl, methyldiethylsilyl, and triphenylgermyl, or $(C_5H_{4-x}R_x)$ is a cyclopentadienyl ring in which two adjacent R substituents are joined to form a ring to give an indenyl or tetrahydroindenyl ligand;

$(JR'_{z-2})$ is a heteroatom ligand selected from the group consisting of t-butylamido, phenylamido, p-n-butylphenylamido, cyclohexylamido, perfluorophenylamido, n-butylamido, methylamido, ethylamido, n-propylamido, isopropylamido, benzylamido, t-butylphosphido, ethylphosphido, phenylphosphido and cyclohexylphosphido, and "z" is 3;

each Q is, independently, selected from the group consisting of hydride, methyl, ethyl, propyl, butyl, amyl, hexyl, heptyl, octyl, nonyl, decyl, cetyl, phenyl, chloro, bromo, fluoro, iodo, methoxy, ethoxy, propoxy, butoxy, phenoxy, methylphenoxy, dimethylamido, diethylamido, methylethylamido, dibutylamido, dipropylamido, diphenylamido, diphenylphosphido, dicyclohexylphosphido, diethylphosphido, and dimethylphosphido;

T is a covalent bridging group selected from the group consisting of dialkyl, alkylaryl or diaryl silicon or germanium radicals; and "L" is a neutral Lewis base where "w" denotes the number 0 or 1;

comprising reacting a $d^0$ Group IV B transition metal halide with a salt containing an anion of the formula $((C_5H_{4-x}R_x)-T-(JR'_{z-2}))^{-2}$ and either two cations from Group I A or one cation from Group II A of the Periodic Table of Elements.

17. A process for producing a compound represented by the general formula:

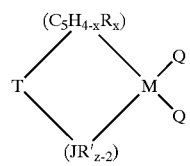

wherein M is Zr, Hf or Ti;

$(C_5H_{4-x}R_x)$ is a cyclopentadienyl ring which is substituted with from zero to four substituent groups R, "x" is 0, 1, 2, 3 or 4 denoting the degree of substitution, and each substituent group R is, independently, a radical selected from the group consisting of halogen radicals, $C_1-C_{20}$ hydrocarbyl radicals, substituted $C_1-C_{20}$ hydrocarbyl radicals where one or more hydrogen atoms is replaced by a halogen radical or $(C_5H_{4-x}R_x)$ is a cyclopentadienyl ring in which two adjacent R substituents are joined to form a ring to give an indenyl or tetrahydroindenyl ligand;

$(JR'_{z-2})$ is a heteroatom ligand selected from the group consisting of t-butylamido, phenylamido, p-n-butylphenylamido, cyclohexylamido, perfluorophenylamido, n-butylamido, methylamido, ethylamido, n-propylamido, isopropylamido, benzylamido, t-butylphosphido, ethylphosphido, phenylphosphido and cyclohexylphosphido, and "z" is 3;

each Q is, independently, selected from the group consisting of hydride, methyl, ethyl, propyl, butyl, amyl, hexyl, heptyl, octyl, nonyl, decyl, cetyl, phenyl, chloro, bromo, fluoro, iodo, methoxy, ethoxy, propoxy, butoxy, phenoxy, methylphenoxy, dimethylamido, diethylamido, methylethylamido, dibutylamido, dipropylamido, diphenylamido, diphenylphosphido, dicyclohexylphosphido, diethylphosphido, and dimethylphosphido; and T is a covalent bridging group selected from the group consisting of dimethylsilyl, diethylsilyl, di-n-propylsilyl, diisopropylsilyl, di-n-butylsilyl, di-t-butylsilyl, di-n-hexylsilyl, methylphenylsilyl, ethylmethylsilyl, diphenylsilyl, n-hexylmethylsilyl, cyclopentamethylenesilyl, cyclotetramethylenesilyl, cyclotrimethylenesilyl, dimethylgermyl, diethylgermyl, methylene, dimethylmethylene, diethylmethylene, ethylene, dimethylethylene, diethylethylene and dipropylethylene;

comprising reacting a $d^0$ Group IV B transition metal halide with a salt containing an anion of the formula $((C_5H_{4-x}R_x)-T-(JR'_{z-2}))^{-2}$ and either two cations from Group I A or one cation from Group II A of the Periodic Table of Elements.

18. A process for producing a compound represented by the general formula:

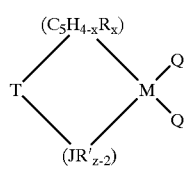

wherein M is Zr, Hf or Ti;

$(C_5H_{4-x}R_x)$ is a cyclopentadienyl ring which is substituted with from zero to four substituent groups R, "x" is 0, 1, 2, 3 or 4 denoting the degree of substitution, and each substituent group R is, independently, a radical selected from the group consisting of methyl, ethyl, propyl, butyl, octyl, benzyl, phenyl, trimethylgermyl, trimethylstannyl, triethylplumbyl, triflouromethyl, trimethylsilyl, triethylsilyl, ethyldimethylsilyl, methyldiethylsilyl, and triphenylgermyl, or $(C_5H_{4-x}R_x)$ is a cyclopentadienyl ring in which two adjacent R substituents are joined to form a ring to give an indenyl or tetrahydroindenyl ligand;

$(JR'_{z-2})$ is a heteroatom ligand selected from the group consisting of t-butylamido, phenylamido, p-n-butylphenylamido, cyclohexylamido, perfluorophenylamido, n-butylamido, methylamido, ethylamido, n-propylamido, isopropylamido, benzylamido, t-butylphosphido, ethylphosphido, phenylphosphido and cyclohexylphosphido, and "z" is 3;

each Q is, independently, selected from the group consisting of hydride, methyl, ethyl, propyl, butyl, amyl, hexyl, heptyl, octyl, nonyl, decyl, cetyl, phenyl, chloro, bromo, fluoro, iodo, methoxy, ethoxy, propoxy, butoxy, phenoxy, methylphenoxy, dimethylamido, diethylamido, methylethylamido, dibutylamido, dipropylamido, diphenylamido, diphenylphosphido, dicyclohexylphosphido, diethylphosphido, and dimethylphosphido; and T is a covalent bridging group selected from the group consisting of dimethylsilyl, diethylsilyl, di-n-propylsilyl, diisopropylsilyl, di-n-butylsilyl, di-t-butylsilyl, di-n-hexylsilyl, methylphenylsilyl, ethylmethylsilyl, diphenylsilyl, n-hexylmethylsilyl, cyclopentamethylenesilyl, cyclotetramethylenesilyl, cyclotrimethylenesilyl, dimethylgermyl, diethylgermyl, methylene, dimethylmethylene, diethylmethylene, ethylene, dimethylethylene, diethylethylene and dipropylethylene;

comprising reacting a $d^0$ Group IV B transition metal halide with a salt containing an anion of the formula $((C_5H_{4-x}R_x)-T-(JR'_{z-2}))^{-2}$ and either two cations from Group I A or one cation from Group II A of the Periodic Table of Elements.

19. The process of claims 1, 2, 3, 4, 5, 12, 13, 14, 15, 16, 17, or 18 wherein M is Zr.

20. The process of claims 1, 2, 3, 4, 5, 12, 13, 14, 15, 16, 17, or 18 wherein M is Hf.

21. The process of claims 1, 2, 3, 4, 5, 12, 13, 14, 15, 16, 17, or 18 wherein M is Ti.

* * * * *